US012704650B2

(12) United States Patent
Labella et al.

(10) Patent No.: US 12,704,650 B2
(45) Date of Patent: Aug. 11, 2026

(54) SYSTEM AND METHOD FOR CRYSTAL-TO-CHANNEL COUPLING

(71) Applicant: THE RESEARCH FOUNDATION FOR THE STATE UNIVERSITY OF NEW YORK, Albany, NY (US)

(72) Inventors: Andrew Labella, Stony Brook, NY (US); Amirhossein Goldan, Stony Brook, NY (US); Eric Peterson, Stony Brook, NY (US); Wei Zhao, East Setauket, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 432 days.

(21) Appl. No.: 18/024,569

(22) PCT Filed: Sep. 3, 2021

(86) PCT No.: PCT/US2021/048998
§ 371 (c)(1),
(2) Date: Mar. 3, 2023

(87) PCT Pub. No.: WO2022/051579
PCT Pub. Date: Mar. 10, 2022

(65) Prior Publication Data

US 2023/0358901 A1 Nov. 9, 2023

Related U.S. Application Data

(60) Provisional application No. 63/074,294, filed on Sep. 3, 2020.

(51) Int. Cl.

| | |
|---|---|
| ***A61B 6/03*** | (2006.01) |
| ***G01T 1/164*** | (2006.01) |
| ***G01T 1/20*** | (2006.01) |

(52) U.S. Cl.
CPC ........ *G01T 1/20184* (2020.05); *G01T 1/1647* (2013.01); *A61B 6/037* (2013.01)

(58) Field of Classification Search
CPC .... A61B 6/037; G01T 1/1647; G01T 1/20184
See application file for complete search history.

(56) References Cited

U.S. PATENT DOCUMENTS 5,391,878 A 2/1995 Petroff
7,129,979 B1 10/2006 Lee
(Continued)

FOREIGN PATENT DOCUMENTS

CN 102782524 A 11/2012
CN 110988842 A 4/2020
(Continued)

OTHER PUBLICATIONS

Extended European search report dated Jul. 12, 2024 received in European Patent Application No. 21865161.0.
(Continued)

*Primary Examiner* — Mark R Gaworecki
(74) *Attorney, Agent, or Firm* — Scully, Scott, Murphy & Presser, P.C.

(57) ABSTRACT

A multiplexing scheme, a system for reading out signals from an optical sensor array, particle detection devices and systems are provided. For example, the optical sensor array may comprise plurality of optical sensors arranged in rows and columns. In the multiplexing scheme, a readout ASIC may be electrically connected to the plurality of optical sensors via a plurality of first channels and a plurality of second channels. Each first channel may be electrically connected to a subset of optical sensors in a corresponding row of the optical sensor array, where there may be at least one optical sensor between connections. Each second channel may be electrically connected to a subset of optical
(Continued)

sensors in a corresponding column of the optical sensor array, where there may be at least one optical sensor between connections.

20 Claims, 22 Drawing Sheets

(56) References Cited

U.S. PATENT DOCUMENTS

| | | | |
|---|---|---|---|
| 7,859,581 | B2 | 12/2010 | Guidash |
| 8,405,038 | B2 | 3/2013 | Bouhnik et al. |
| 11,112,278 | B2 | 9/2021 | Lo et al. |
| 11,454,730 | B2 | 9/2022 | Goldan et al. |
| 2012/0061577 | A1 | 3/2012 | Oleinik et al. |
| 2013/0153776 | A1 | 6/2013 | Wieczorek et al. |
| 2014/0027611 | A1 | 1/2014 | Patel |
| 2016/0223690 | A1 | 8/2016 | Uchida |
| 2019/0219713 | A1 | 7/2019 | Booker et al. |
| 2020/0092504 | A1 | 3/2020 | Allen et al. |
| 2022/0120923 | A1 | 4/2022 | Goldan et al. |
| 2023/0375731 | A1 | 11/2023 | Labella et al. |

FOREIGN PATENT DOCUMENTS

| | | | |
|---|---|---|---|
| JP | 2004032750 | A | 1/2004 |
| JP | 5008031 | B2 | 8/2012 |
| JP | 5067753 | B2 | 11/2012 |
| JP | 2013516609 | A | 5/2013 |
| JP | 2017072573 | A | 4/2017 |
| JP | 2018023096 | A | 2/2018 |
| JP | 2019522937 | A | 8/2019 |
| JP | 2020526754 | A | 8/2020 |
| JP | 2023028058 | A | 3/2023 |
| JP | 2024026475 | A | 2/2024 |
| JP | 7809699 | B2 | 2/2026 |
| JP | 2026016365 | A | 2/2026 |
| KR | 20090013711 | A | 2/2009 |
| KR | 20200024914 | A | 3/2020 |
| KR | 20210046697 | A | 4/2021 |
| WO | 2011090530 | A2 | 7/2011 |
| WO | 2020033749 | A1 | 2/2020 |
| WO | 2021050814 | A1 | 3/2021 |
| WO | 2021146559 | A1 | 7/2021 |
| WO | 2021173708 | A1 | 9/2021 |
| WO | 2022051506 | A1 | 3/2022 |
| WO | 2022163710 | A1 | 8/2022 |
| WO | 2022220287 | A1 | 10/2022 |

OTHER PUBLICATIONS

International Search Report dated Nov. 30, 2021 issued in PCT/US2021/048998.

Written Opinion dated Nov. 30, 2021 issued in PCT/US2021/048998.

Notice of Reasons for Refusal dated Jul. 15, 2025 received in japanese patent Application No. 2023-514996.

First Office Action dated Jul. 16, 2025 received in Chinese Patent Application No. 202180054304.4.

Office Action dated Mar. 12, 2026 received in Korean Patent Application No. 10-2023-7010856.

Office Action dated Mar. 6, 2026 received in European Patent Application No. 21 865 161.0.

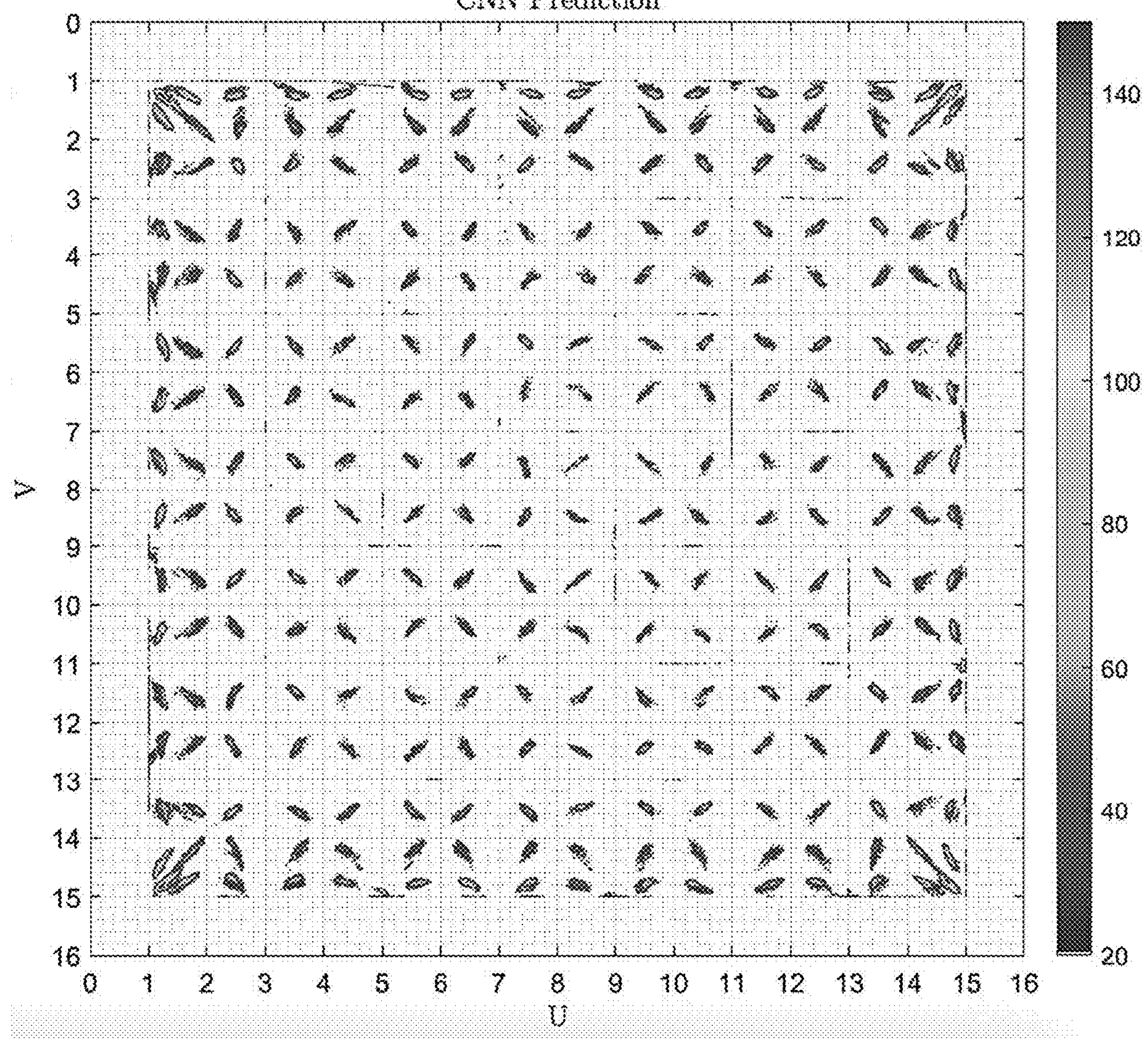
CNN Prediction
V
U
0
1
2
3
4
5
6
7
8
9
10
11
12
13
14
15
16
140
120
100
80
60
40
20

SYSTEM AND METHOD FOR CRYSTAL-TO-CHANNEL COUPLING

CROSS-REFERENCE TO RELATED APPLICATION

This application claims the benefit of and priority to U.S. Provisional Application Ser. No. 63/074,294 filed on Sep. 3, 2020, the entirety of which is incorporated by reference.

STATEMENT REGARDING FEDERALLY SPONSORED RESEARCH

This invention was made with government support under contract no. 808690 awarded by National Science Foundation. The government has certain rights in the invention.

FIELD

This disclosure relates generally to the field of radiation imaging and, in particular, to positron emission tomography (PET).

BACKGROUND

Imaging with PET is a powerful technique used primarily for diagnosis, treatment selection, treatment monitoring and research in cancer and neuropsychiatric disorders. Despite its high molecular specificity, quantitative nature and clinical availability, PET has not been able to achieve its full potential as the go-to molecular imaging modality due in large part to its relatively poor spatial resolution. Several attempts have been tried to achieve high resolution PET, including using n-to-1 scintillator modules-to-readout pixel coupling (where n>1) (optical sensor), which enables spatial resolution equal to the size of the scintillator modules without increasing the cost of the readout side (e.g., optical sensor, connectors, readout ASIC). While other attempts including using monolithic scintillator modules with nearest-neighbor positioning algorithms, the n-to-1 coupling light sharing are the most commercially viable option due to their simultaneous depth of interaction (DOI) and time-of-flight (TOF) readout capabilities due to the fact that there is no tradeoff in sensitivity and/or energy resolution.

However, as spatial resolution improves, the amount of data per PET scan greatly increases due to the increased number of voxels. Depth-encoding, which is necessary to mitigate parallax error and fully reap the benefits of high resolution PET, further exacerbates the data size problem since the number of lines-of-response (LORs) increases exponentially as a function of number of DOI bins. Combining high resolution with TOF readout also contributes to larger data size in PET since each channel reads out a timestamp per pixel even though multiple timestamps aren't typically used per event, making this process computationally inefficient.

As the data increases, the number of connections between the optical sensors and readout ASIC increase which in practice will increase the heat generated by the device.

Signal multiplexing, whereby the signals read out by multiple optical sensors (pixels) per event are summed together, has been proposed to reduce the data size and complexity in order to make PET less computationally expensive. However, where the signals are multiplex, solutions must be still able to determine primary optical sensor (pixel) interaction, primary scintillator module interaction and DOI.

In one or more known systems with multiplexing, the detector modules used don't have depth-encoding capabilities (and thus, the multiplexed readout scheme hasn't been shown to work with DOI readout), which is paramount to achieve spatial resolution uniformity at the system-level.

SUMMARY

Accordingly, disclosed is a system for reading out signals from an optical sensor array. The optical sensor array may comprise a plurality of optical sensors arranged in rows and columns. Each optical sensor in the array corresponds to a pixel. The system may comprise a plurality of first channels, a plurality of second channels and a first processor. The first processor may be electrically connected to the plurality of optical sensors via the plurality of first channels and the plurality of second channels. Each first channel may be electrically connected to a subset of optical sensors in a corresponding row of the optical sensor array. There may be at least one optical sensor between connections. Each second channel may be electrically connected to a subset of optical sensors in a corresponding column of the optical sensor array. There may be at least one optical sensor between connections. The first processor may readout signals via the plurality of first channels and the plurality of second channels. The first processor may cause power to be supplied to each of the plurality of optical sensors to bias the optical sensors during a readout. The first processor may be a readout ASIC.

In an aspect of the disclosure, the plurality of first channels may comprise a first row channel and a second row channel. The first row channel may be electrically connected to a subset of optical sensors in a first row of the optical sensor array, and the second row channel may be electrically connected to a subset of optical sensors in a second row of the optical sensor array. The first row may be adjacent to the second row. The subset of optical sensors in the first row may not be in the same columns of the optical sensor array as the subset of optical sensors in the second row.

In an aspect of the disclosure, the plurality of second channels may comprise a first column channel and a second column channel. The first column channel may be electrically connected to a subset of optical sensors in a first column of the optical sensor array, and the second column channel may be electrically connected to a subset of optical sensors in a second column of the optical sensor array. The first column may be adjacent to the second column. The subset of optical sensors in the first column may not be in the same rows of the optical sensor array as the subset of optical sensors in the second column.

In an aspect of the disclosure, the optical sensor array may have M rows and M columns of optical sensors and the plurality of first channels may comprise M row channels and the plurality of second channels may comprises M column channel. M may be an integer multiple of 2. For example, the optical sensor array may be 8×8.

Also disclosed is a particle detection device which may comprise a system for reading out signals from an optical sensor array as described above. The particle detection device may further comprise a scintillator array and a segmented light guide. The scintillator array may comprise a second plurality of scintillator modules. The second plurality of scintillator modules may be greater than the plurality of optical sensors. Multiple scintillator modules may be in contact with a respective optical sensor at a first end of the respective scintillator modules. The segmented light guide may comprise a plurality of prismatoid segments. The segmented light guide may be in contact with a second end of the second plurality of scintillator modules. Each prismatoid segment may be in contact with scintillator modules that are in contact with at least two different optical sensors. The at least two different optical sensors may be adjacent optical sensors. Each prismatoid segment may be configured to redirect particles between scintillator modules in contact with the respective prismatoid segment.

In an aspect of the disclosure, the segments may have three different designs such as center prismatoid segments, edge prismatoid segments and corner prismatoid segments. The center prismatoid segments may be in contact with scintillator modules that are in contact with four adjacent optical sensors. The corner prismatoid segments may be in contact with scintillator modules that are in contact with three adjacent optical sensors. The edge prismatoid segments may be in contact with scintillator modules that are in contact with two adjacent optical sensors.

Also disclosed is a particle detection system having the particle detection device describe above. The particle detection system may further comprise a second processor in communication with the first processor. The second processor may be configured identify a subset of channels having the highest signals per event and determine at least one of a primary interaction pixel for the event, a primary interaction scintillator module for the event or a depth of interaction of the event using signals from the identified subset of channels.

In an aspect of the disclosure, the second processor may be configured to determine the depth of interaction of the event based on a ratio of the signal from the channel having the highest signal per event and a sum of the signals from each of the subset of channels having the highest signals per event, respectively. In other aspects of the disclosure, the depth of interaction may be calculated using demultiplexed signals.

In an aspect of the disclosure, the second processor may be configured to determine the primary interaction pixel for the event based on positional relationship between the subset of channels to unique identify adjacent optical pixels and the channel having the highest signal per event to identify the primary interaction pixel from the identified adjacent optical pixels.

In an aspect of the disclosure, the second processor may be configured to determine the primary interaction scintillator module for the event based on an energy weighted average. In an aspect of the disclosure, the energy weighted average may be calculated using the demultiplexed signals.

In an aspect of the disclosure, the second processor may be configured to demultiplex signals from the plurality of first channels and the plurality of second channels using a stored machine learned model using the signals from the plurality of first channels and the plurality of second channels as input. In some aspects, the machine learned model may be based on a convolutional neural network.

In other aspects of the disclosure, the second processor may be configured to demultiplex signals from the plurality of first channels and the plurality of second channels using a stored look up table.

In an aspect of the disclosure, the second processor may be configured to determine the primary interaction scintillator module using relative values of the signals from the identified subset of channels and the identified adjacent optical pixels.

In an aspect of the disclosure, the number of channels in the subset of channels may be based on the location of the primary optical sensor in the optical sensor array. For example, the number of channels in the subset when the primary optical sensor is a corner optical sensor in the optical array may be three, the number of channels in the subset when the primary optical sensor is an edge optical sensor may be two and the number of channels in the subset when the primary optical sensor is a center optical sensor in the array may be four.

In an aspect of the disclosure, there may be a four-to-one scintillator module to optical sensor coupling. In other aspects, there may be a nine-to-one scintillator module to optical sensor coupling.

Also disclosed is a method of multiplexing signals from an optical sensor array. The optical sensor array may comprise a plurality of optical sensors arranged in rows and columns. Each optical sensor in the array corresponds to a pixel. The method may comprise for each row in the optical sensor array connecting a first channel to a subset of optical sensors in the row, respectively, and for each column in the optical sensor array connecting a second channel to a subset of the optical sensors in the column, respectively. There may be at least one optical sensor between connections. The method may further comprise connecting each of the first channels and each of the second channels to a processor.

In an aspect of the disclosure, the subset of optical sensors in a row connected to a first channel for a first row may be offset by column to the subset of optical sensors in a row connected to a first channel for a second row where the first row and the second row are adjacent.

In an aspect of the disclosure, the subset of optical sensors in a column connected to a second channel for a first column may be offset by row to the subset of optical sensors in a column connected to a second channel for a second column, where the first column and the second column are adjacent.

BRIEF DESCRIPTION OF THE DRAWINGS

FIG. 9A and FIG. 9B illustrate a comparison between a ground truth and demultiplexing the multiplexed signals using the machine learning model in accordance with aspects of the disclosure for a 4-to-1 scintillator module to optical sensor coupling;

DETAILED DESCRIPTION

Figure 1A:
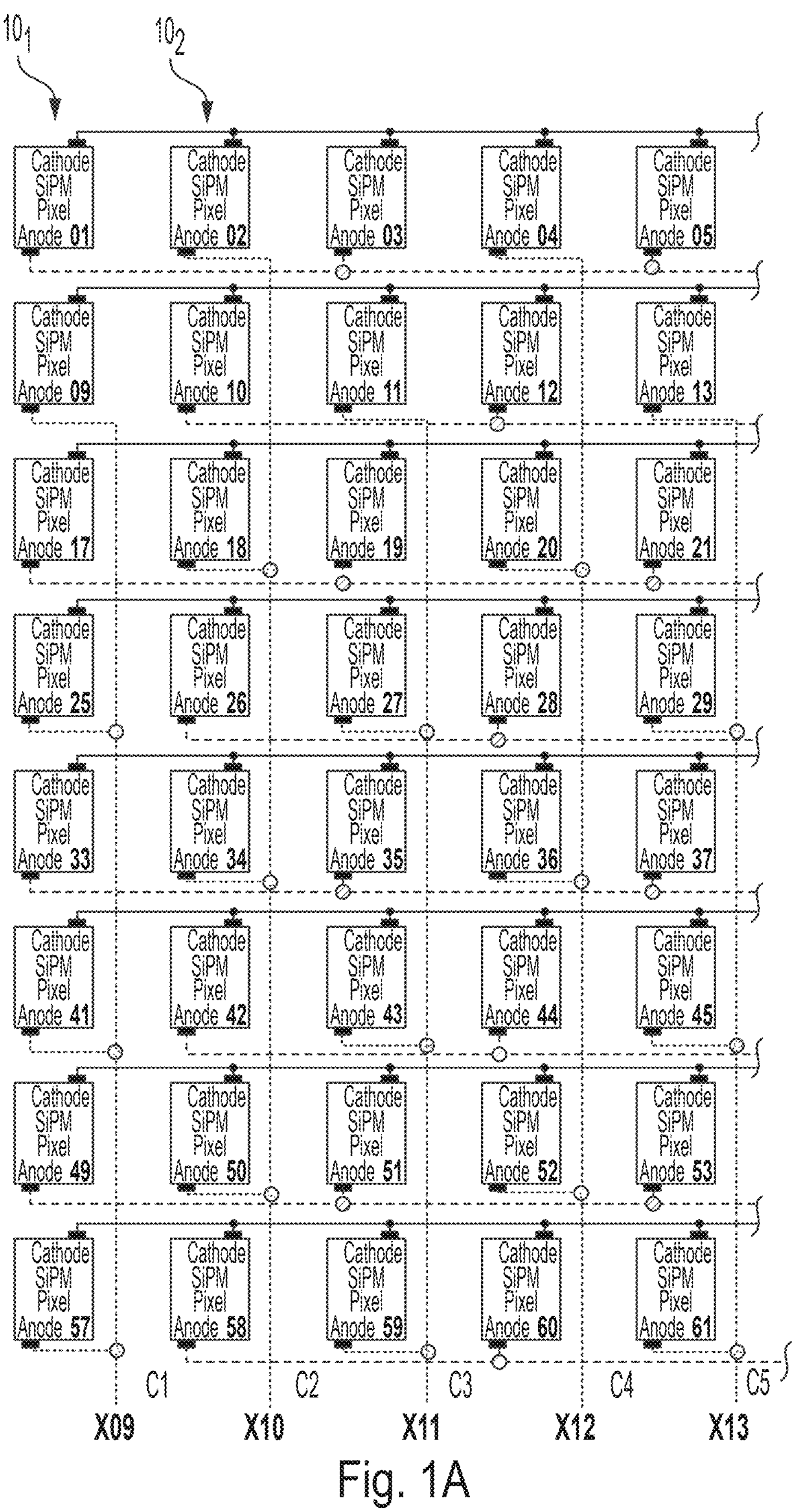
FIG. 1A illustrates a multiplexing scheme in accordance with aspects of the disclosure having anodes of the optical sensor multiplexed to provide energy information.
Figure 1A:
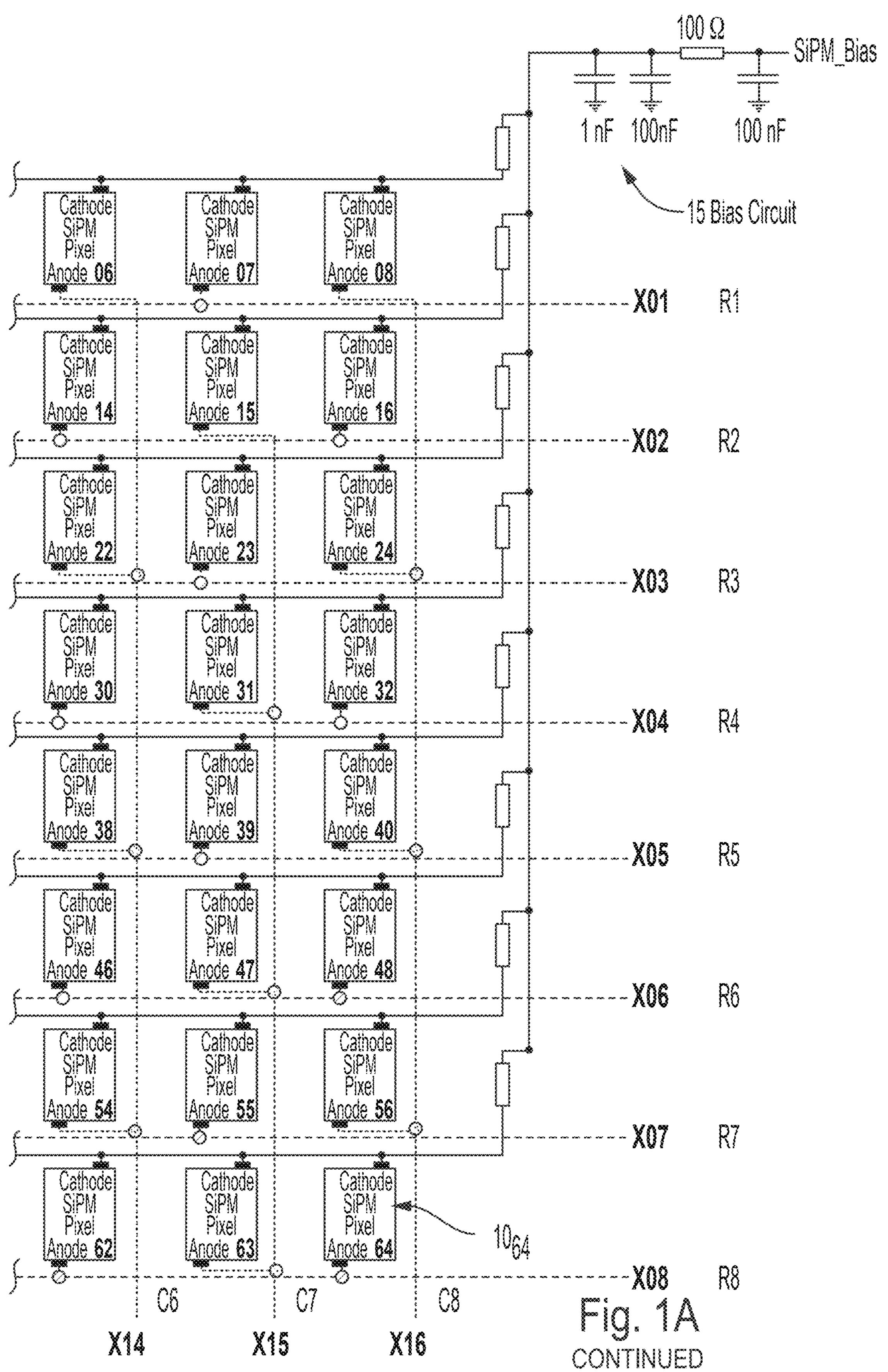

Disclosed is a multiplexing scheme that takes advantage of deterministic light sharing which is enabled using a segmented light guide such as disclosed in U.S. Pat. Pub. No. 2020/0326434 which is incorporated by reference. The particle detection system (and device) described herein has a single-ended readable (with depth-encoding) that has a specialized pattern of segments of a segmented light guide. The light guide has prismatoid light guide segments which will be described in detail with respect to at least FIG. 3A. In accordance with aspects of the disclosure, the segmented light guide 200 has at least three distinct prismatoid designs, e.g., center prismatoid 162, corner prismatoid 166 and edge prismatoid 168. The prismatoids are designed to mitigate edge and corner artifacts, thereby achieving a uniform crystal identification performance, even when using the multiplexing scheme described herein.

Light sharing between scintillator modules 205 is confined to only scintillator modules 205 belonging to adjacent or neighboring optical sensors 10 (e.g., nearest neighbors) to create a deterministic and anisotropic inter-scintillator module light sharing pattern and maximize signal-to-background ratio on the optical sensors 10 to improve both energy and DOI resolutions.

Due to the deterministic light sharing pattern, only a subset of optical sensors 10 (pixels) from nearest neighboring optical sensors (pixels) are required to accurately perform primary optical sensor interaction and DOI (and estimate the primary scintillator module). This is because the relevant signals will be contained within the optically isolated prismatoid segments.

FIG. 1A illustrates an example of a multiplexing scheme in accordance with aspects of the disclosure. As shown in FIG. 1A, the optical sensors $\mathbf{10}_1$-$\mathbf{10}_{64}$ (collectively 10) (e.g., optical sensor array 210) is arranged in a plurality of rows and a plurality of columns. In the example depicted in FIG. 1A, the optical sensor array 210 is for an 8×8 readout array. However, the readout array is not limited to 8×8 and may be other dimensions such as 4×4 or 16×16. In some aspects, the readout array may be an integer multiple of two. The two-dimensional array may be formed in a plane orthogonal to a longitudinal axis of the scintillator module. In an aspect of the disclosure, the optical sensors 10 may be a silicon photomultiplier (SiPM). In other aspects of the disclosure, the optical sensors 10 may be avalanche photodiodes (APDs), single-photon avalanche (SPADs), photomultiplier tubes (PMTs), silicon avalanche photodiodes (SiAPDs). These are non-limiting examples of solid state detectors which may be used. The number of optical sensors 10 (pixels) in the device may be based on the application and size of a PET system. In FIG. 1A, the optical sensors 10 are labeled "SiPM Pixel". The two digit number in the bottom right corner of each pixel represents a pixel number. For example, "01" represents the first pixel and "64" represents the last pixel. The numbers are for descriptive purposes only.

Each optical sensor 10 has an anode and cathode. In FIG. 1A, the cathode is shown on the top of the pixel and the anode is shown on the bottom of each pixel. In an aspect of the disclosure, a bias may be supplied to the cathode via a bias circuit 15. The bias circuit 15 may comprise one or more capacitors and one or more resistors. In FIG. 1A, three capacitors are shown. However, the bias circuit 15 is not limited to three. One resistor is shown between the capacitors. However, the bias circuit 15 is not limited to one resistor between the capacitors. Another resistor may be positioned in series with a row of optical sensors R1-R8. In accordance with aspects of the disclosure, there are a plurality of horizontal channels (X01-X08) (also referred to herein a first channels). The number of horizontal channels is equal to the number of rows R1-R8 in the array, e.g., one-to-one relationship.

In an aspect of the disclosure, each horizontal channel is connected to a subset of the optical sensors of the row (as shown in FIG. 1A at the anode). There is at least one optical sensor 10 (pixel) between the optical sensors connected to the same horizontal channel. For example, in channel X01 (for row R1), optical sensors $\mathbf{10}_1$, $\mathbf{10}_3$, $\mathbf{10}_5$, $\mathbf{10}_7$ are connected to X01 (for illustrative purposes not all pixels/optical sensors are specifically labelled with a reference 10). Optical sensors $\mathbf{10}_2$, $\mathbf{10}_4$, $\mathbf{10}_6$, $\mathbf{10}_8$ are not connected to X01. In other aspects of the disclosure, Optical sensors $\mathbf{10}_2$, $\mathbf{10}_4$, $\mathbf{10}_6$, $\mathbf{10}_8$ may be connected to X01 and optical sensors $\mathbf{10}_1$, $\mathbf{10}_3$, $\mathbf{10}_5$, $\mathbf{10}_7$ may not be connected to X01.

In an aspect of the disclosure, the subset of optical sensors in a row connected to a horizontal channel is offset from the subset of optical sensors in adjacent row connected to its horizontal channel, by column. For example, optical sensors $\mathbf{10}_1$, $\mathbf{10}_3$, $\mathbf{10}_5$, $\mathbf{10}_7$ which are connected to channel X01, are in columns C1, C3, C5 and C7, respectively. Therefore, optical sensors $\mathbf{10}_9$, $\mathbf{10}_{11}$, $\mathbf{10}_{13}$, $\mathbf{10}_{15}$, which are also in columns C1, C3, C5 and C7 may not be connected to channel X02, but rather optical sensors $\mathbf{10}_{10}$, $\mathbf{10}_{12}$, $\mathbf{10}_{14}$, $\mathbf{10}_{16}$, which are in columns C2, C4, C6 and C8.

In accordance with aspects of the disclosure, there are a plurality of vertical channels (X09-X16) (also referred to herein a second channels). The number of vertical channels is equal to the number of columns C1-C8 in the array, e.g., one-to-one relationship.

In an aspect of the disclosure, each vertical channel is connected to a subset of the optical sensors of the column. There is at least one optical sensor 10 (pixel) between the optical sensors connected to the same vertical channel. For example, in channel X09 (for column C1), optical sensors $\mathbf{10}_9$, $\mathbf{10}_{25}$, $\mathbf{10}_{41}$, $\mathbf{10}_{57}$ are connected to X09. Optical sensors $\mathbf{10}_1$, $\mathbf{10}_{17}$, $\mathbf{10}_{33}$, $\mathbf{10}_{49}$ are not connected to channel X09. In other aspects of the disclosure, optical sensors $\mathbf{10}_1$, $\mathbf{10}_{17}$, $\mathbf{10}_{33}$, $\mathbf{10}_{49}$ may be connected to channel X09 and optical sensors $\mathbf{10}_9$, $\mathbf{10}_{25}$, $\mathbf{10}_{41}$, $\mathbf{10}_{57}$ may not be connected to X09.

In an aspect of the disclosure, the subset of optical sensors in a column connected to a vertical channel is offset from the subset of optical sensors in column row connected to its vertical channel, by row. For example, optical sensors $\mathbf{10}_9$, $\mathbf{10}_{25}$, $\mathbf{10}_{41}$, $\mathbf{10}_{57}$ which are connected to channel X09, are in rows R2, R4, R6 and R8 respectively. Therefore, optical sensors $\mathbf{10}_{10}$, $\mathbf{10}_{26}$, $\mathbf{10}_{42}$, $\mathbf{10}_{58}$ (in Columns C2) which are also in row R2, R4, R6 and R8 may not be connected to channel X10, but rather optical sensors $\mathbf{10}_2$, $\mathbf{10}_{18}$, $\mathbf{10}_{34}$, $\mathbf{10}_{50}$, which are in rows R1, R3, R5 and R7.

The channels are connected such that adjacent pixels in any direction are not connected to the same channel. Each optical sensor is only connected to one channel. The use of "vertical" or "horizontal" is for descriptive purposes only.

These channels (e.g., X01-X16) are energy channels, which are used to determine primary optical sensor interaction, primary scintillator module interaction and DOI. In other aspects of the disclosure, there may be addition channels for other determinations such as TOF (timing channels). Examples of these additional channels are shown in FIG. 1C.

Figure 1B:
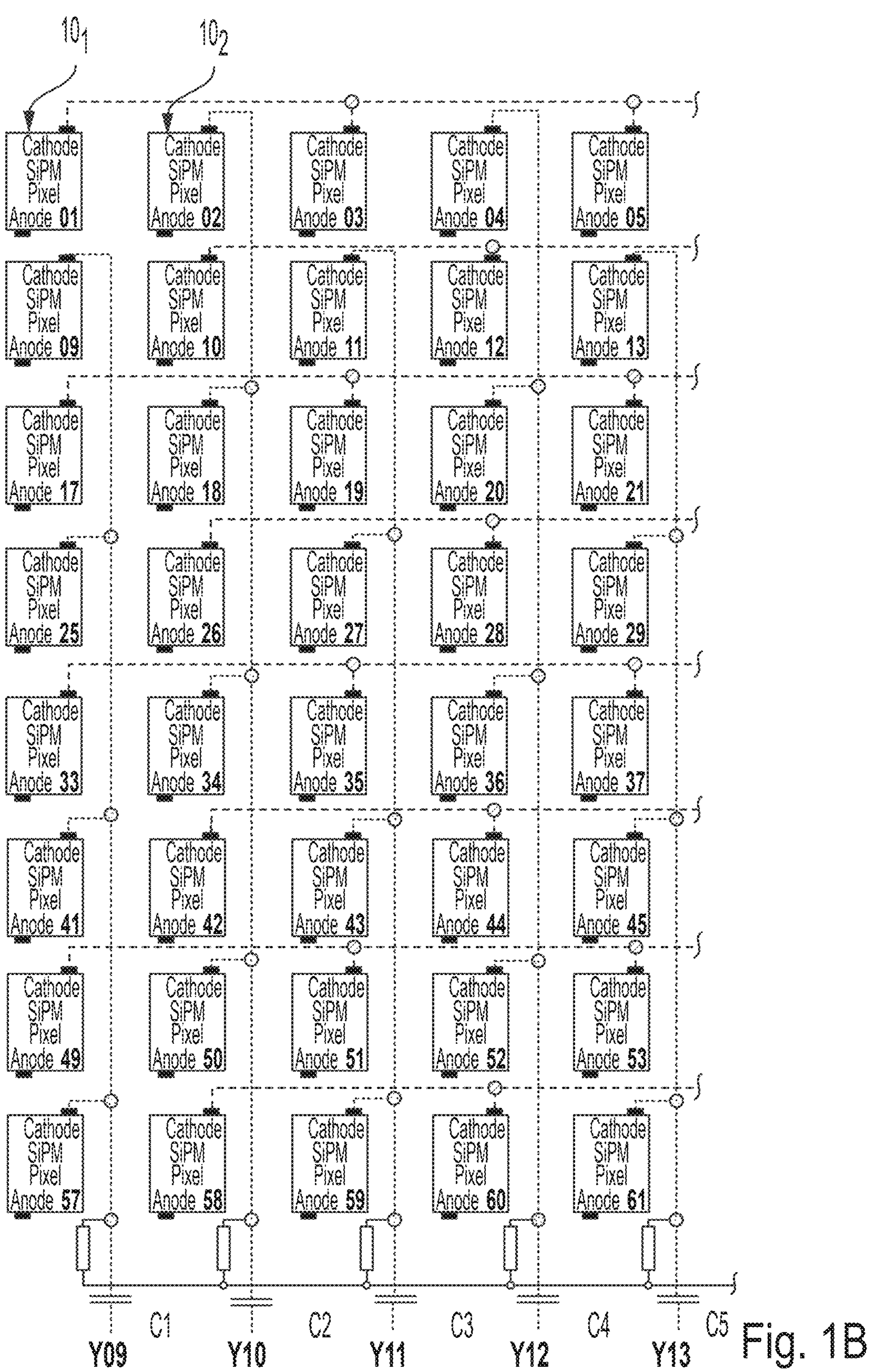
FIG. 1B illustrates a multiplexing scheme in accordance with aspects of the disclosure having cathodes of the optical sensor multiplexed to provide energy information.
Figure 1B:
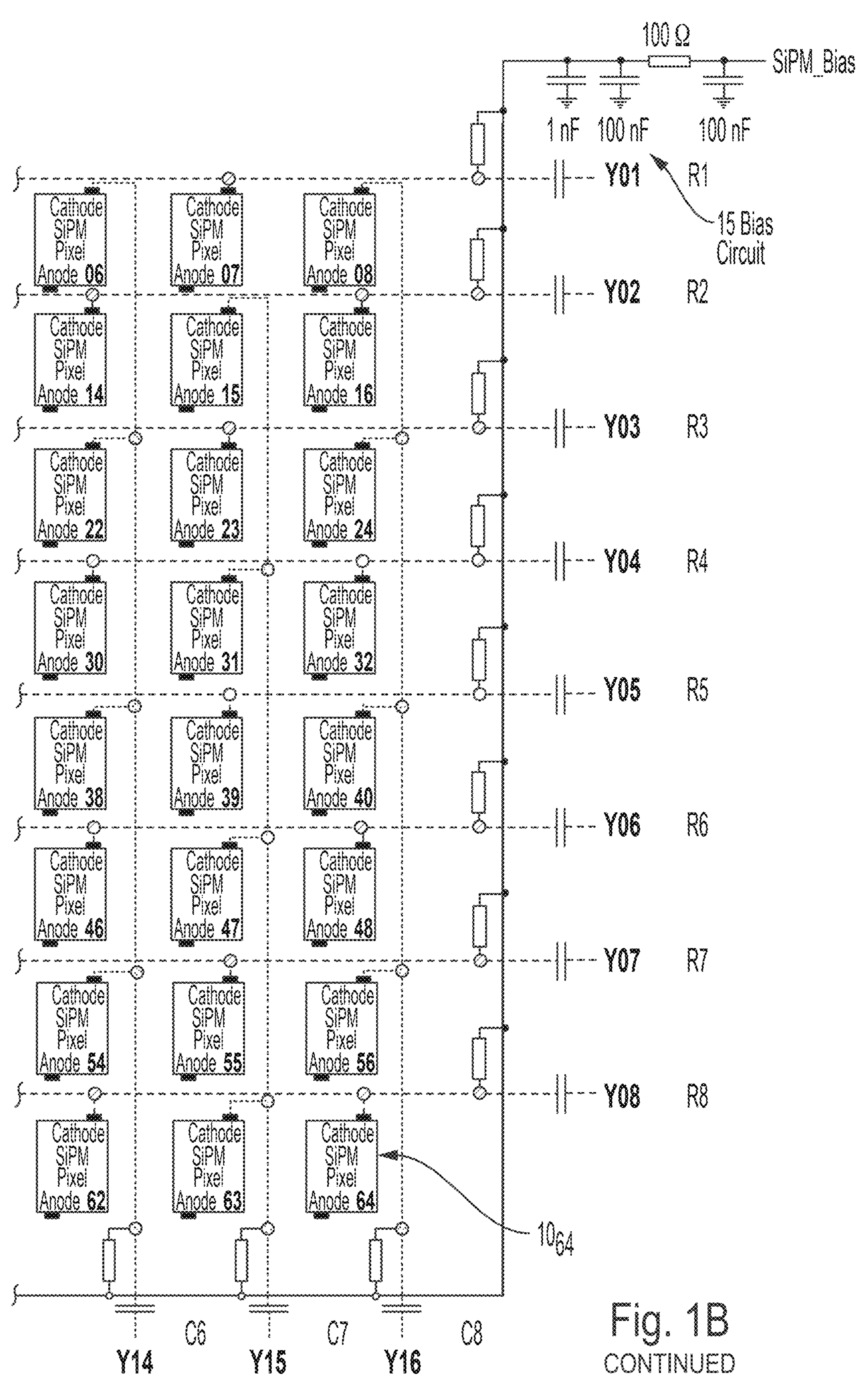

In other aspects of the disclosure, the energy channels (e.g., Y01-Y16) may be connected to the cathode such as shown in FIG. 1B. In FIG. 1B, both the bias and the energy channels are coupled to the cathode. In FIG. 1B, the anode may be connected to ground. In other aspects, since the number of channels is reduced and the anodes are connected to ground, anode connections may be used for timestamping (Timing). For example, FIG. 1C shows optical sensors $\mathbf{10}_1$, $\mathbf{10}_3$, $\mathbf{10}_5$ $\mathbf{10}_7$ for one energy channel. The signals from the cathodes are multiplexed to form one energy channel, e.g., Y01. The signals are integrated by integrator 30 to provide the energy for event (ASIC_Energy_01). It is noted that the integrator 30 for each energy channel (e.g., X01-X16 in FIG. 1A) and (e.g., Y01-Y16 in FIG. 1B) is omitted in FIGS. 1A and 1B. As shown in FIG. 1C, three comparators 20 are connected to the multiplexed output of the anodes of the optical sensors $\mathbf{10}_1$, $\mathbf{10}_3$, $\mathbf{10}_5$ $\mathbf{10}_7$. Each comparator 20 is associated with a different voltage threshold. V_th1, V_th2 and V_th3. When the multiplexed voltage exceeds the respective threshold, the respective comparator 20 will output a change (e.g., Z01_T1, Z01_T2 and Z01_T3). The time of change can be used as a timestamp. The three different timestamps may be used to calculate a rate of change.

Figure 1C:
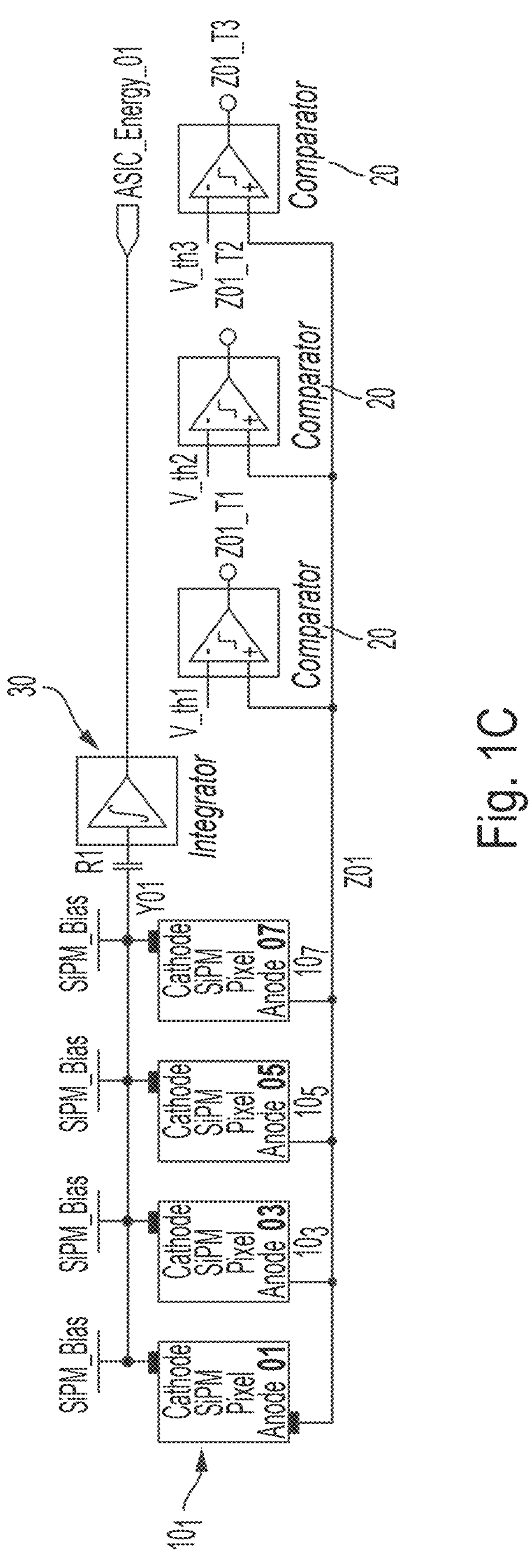
FIG. 1C illustrates a multiplexing scheme for one energy channel in accordance with aspects of the disclosure having cathodes of the optical sensor multiplexed to provide energy information and anodes of the optical sensor multiplexed to provide information on timing.

While FIG. 1C shows only one energy channel Y01, the same configuration may apply to the other 15 channels, e.g., Y02-Y16. Other point of connection (combinations) may be used and are not limited to FIGS. 1A-FIG. 1C.

The remaining portion of the disclosure describes channels X01-X16 and multiplexing scheme disclosed in FIG. 1A. However, the disclosure equally applies to channels Y01-Y16 and the multiplexing scheme in FIG. 1B (and FIG. 1C). Each of the channels X01-X16 may be connected to a Readout ASIC 405 (also referred herein as first processor). The Readout ASIC 405 may comprise analog to digital converters for digitalization of the signals from the optical sensor array 210 and circuitry to control the biasing. The readout ASIC 405 may also comprise a communication interface to transmit the digitized signals to a remote computer 400 (also referred herein as second processor) via a synchronization board 410. The synchronization board synchronizes readouts from different detection devices/Readout ASIC in the PET system. In the system shown in FIG. 2B, only one detection device is shown, however, in practice there are a plurality of detection devices connected to the synchronization board 410. Each detection device having the 4-to-1 readout multiplexing 1 described herein. The reflector 215 is omitted from FIG. 2B. However, each detection device would have the reflector 215.

As described above, the deterministic light sharing schemed caused by the segmented light guide 200 guarantees that the inter-scintillator module light sharing only occurs between scintillator modules coupled to the same optically isolated prismatoid light guide.

Figure 2A:
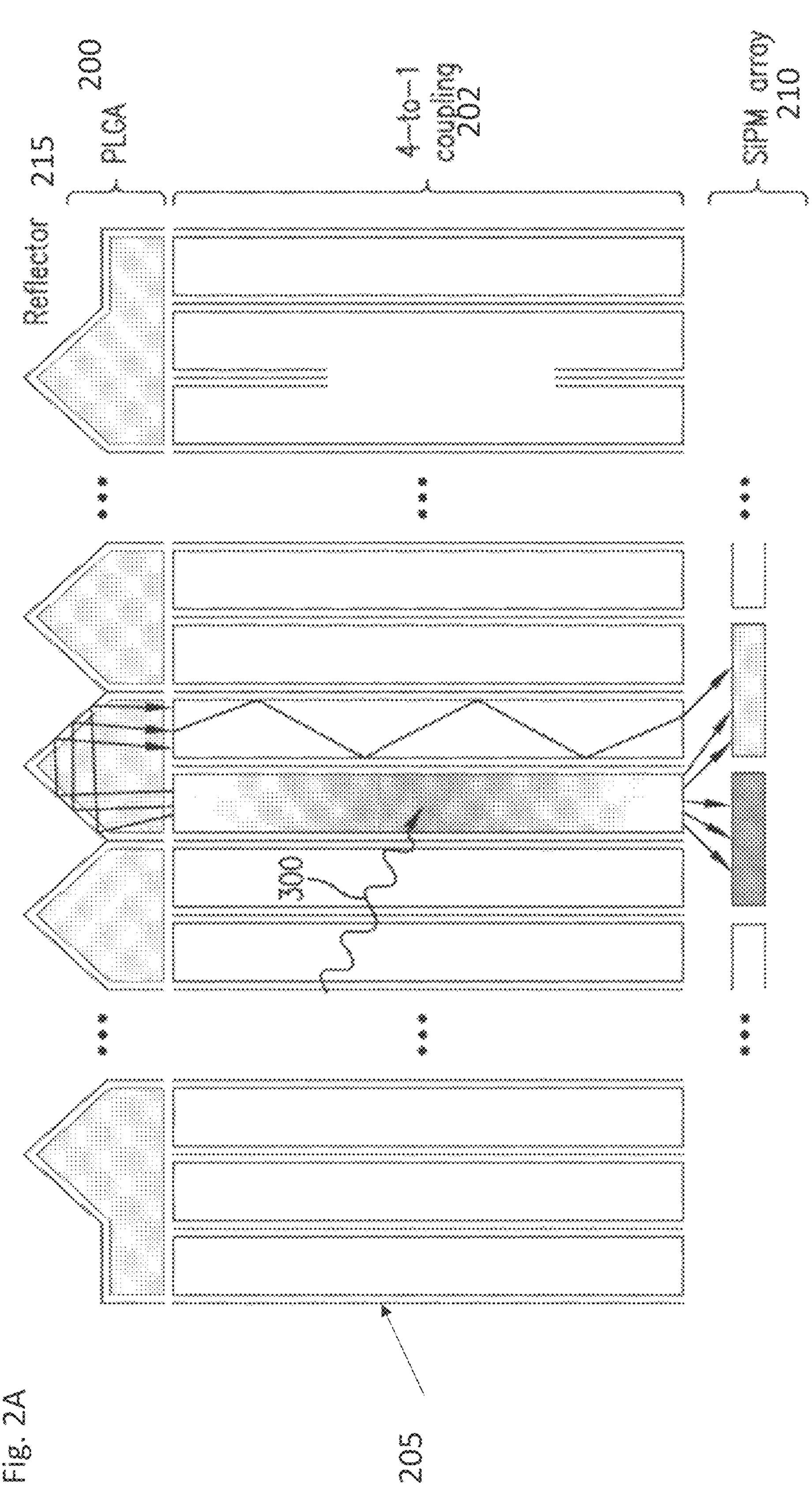
FIG. 2A illustrates a particle detection device having 4-to-1 scintillator module to optical sensor coupling in accordance with aspects of the disclosure.

FIG. 2A illustrates a particle detection device having a 4-to-1 scintillator module to optical sensor coupling 202 in accordance with aspects of the disclosure. Each scintillator module 205 may be fabricated from lutetium-yttrium oxyorthosilicate (LYSO) crystals. The scintillator module 205 is not limited to LYSO and other types of crystals may be used that emits a light photon in the present of incident gamma radiation, such as Lutetium oxyorthosilicate (LSO). In FIG. 2A, the optical sensor array is represented as an SiPM array 210. However, as described above, the array is not limited to an SiPM. The scintillator modules 205 are in contact with a surface of the SiPM array 210 at a first end. While FIG. 2A shows a space between the scintillator modules 205 and the SiPM array 210, in practice, the scintillator modules 205 are attached to the SiPM array 210 via an optical adhesive or epoxy. The optical adhesive or epoxy does not change the path of the particle or light or attenuate the same (if any change, the change is minimal). The space is shown to illustrate the particles travelling from the first end of the scintillator module to the SiPM array (pixel). The scintillator modules 205 are in contact with a surface of the segmented light guide (PLGA 200) on a second end. A reflector 215 is positioned above the PLGA 200. In an aspect of the disclosure, the reflector 215 may comprise barium sulfate $BaS0_4$. In other aspects, the reflector 215 may comprise other reflective materials. In an aspect of the disclosure, a reflector 215 may be used between each of the scintillator modules 205. The reflector 215 may also fill any space between the segments of the segmented light guide 200.

Figure 3A:
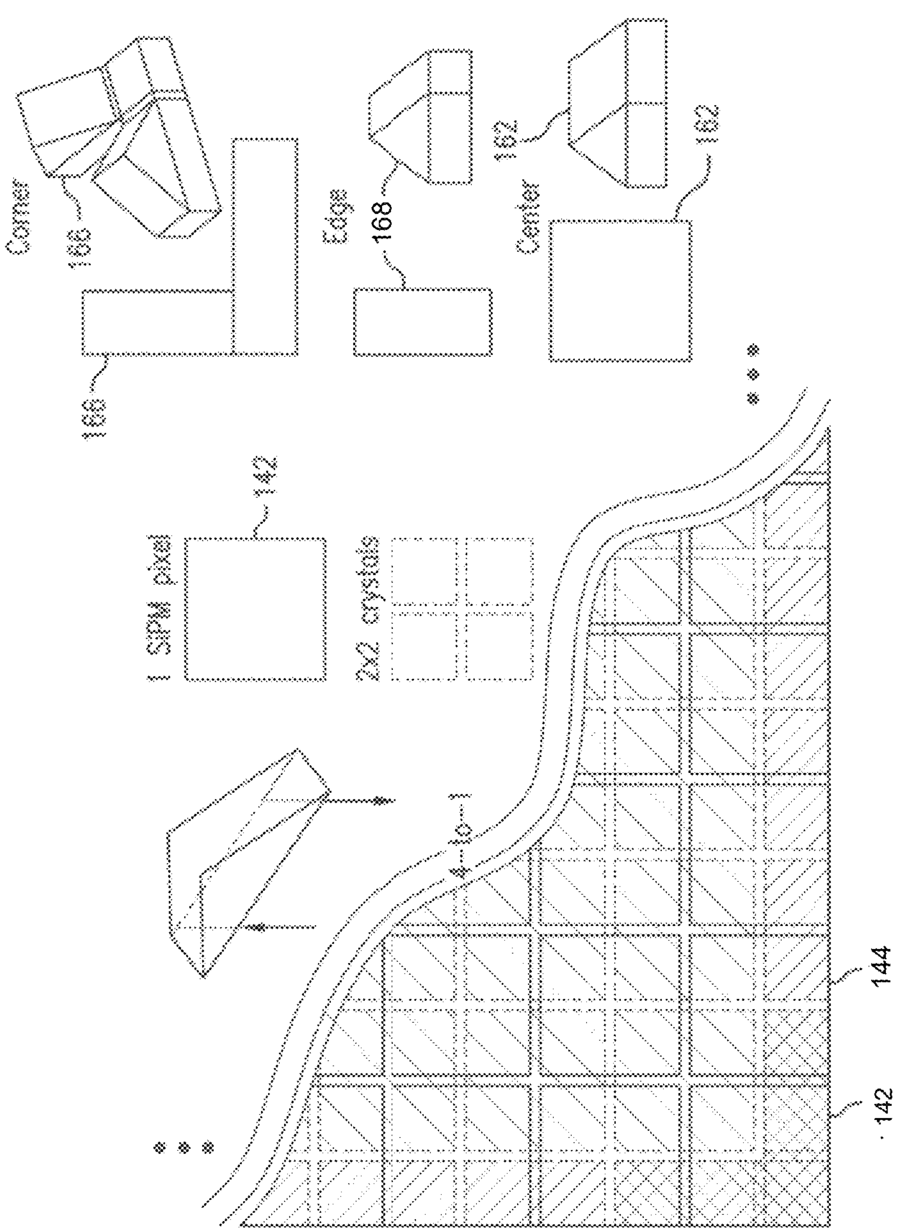
FIG. 3A illustrates a top-down view of a segmented light guide and optical sensors for a 4-to-1 scintillator module to optical sensor coupling, where there are three different designs of segments of the segmented light guide.

FIG. 3A illustrates a view of a segmented light guide and optical sensors for a 4-to-1 scintillator module to optical sensor coupling, where there are three different designs of segments of the segmented light guide. The lower left corner of the figure is a plan view illustrating the relative arrange of scintillator modules (2×2) per optical sensor. Also referred to in FIG. 3A as "crystals". Only a subset of the array is shown for illustrative purposes. The three different designs for the prismatoid segments, e.g., center prismatoid 162, corner prismatoid 166 and edge prismatoid 168, are shown with different hashing. The center prismatoid 162 and edge prismatoid 168 are shown with hashing in opposite directions and the corner prismatoid 166 is shown with intersecting hashing. The upper right corner of FIG. 3A illustrates an example of the three different designs (both a sectional view and a perspective view). The corner prismatoid 166 may be in contact with scintillator modules 205 that are in contact with three different optical sensors (three pixels). The edge prismatoid 168 may be in contact with scintillator modules 205 that are in contact with two different optical sensors (two pixels). The center prismatoid 162 may be in contact with scintillator modules 205 that are in contact with four different optical sensors (four pixels).

Figure 3B:
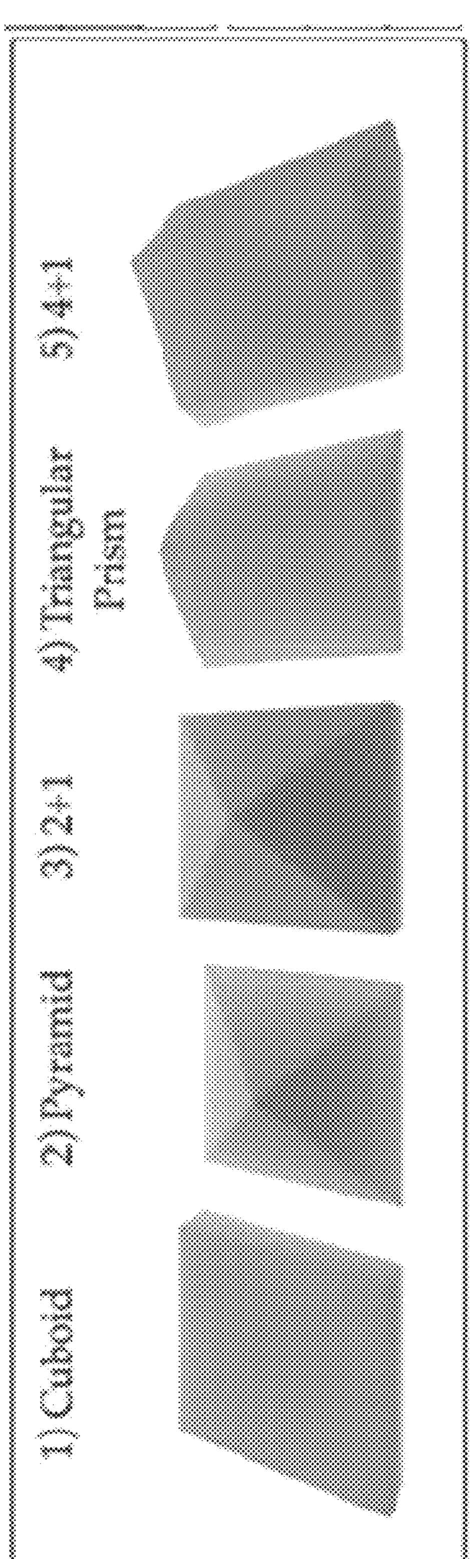
FIG. 3B illustrates examples of 3D views of segments for the segmented light guide in accordance with aspects of the disclosure.

Two adjacent optical sensors are identified using 142 and 144 in FIG. 3A. As shown in FIG. 3A, the prismatoid is substantially triangular in profile shape. However, in other aspect of the disclosure, the prismatoid may be substantially shaped as at least one of at least one prism, at least one antiprism, at least one frustum, at least one cupola, at least one parallelepiped, at least one wedge, at least one pyramid, at least one truncated pyramid, at least one portion of a sphere, at least one cuboid. . . . Examples of certain 3D shapes (five different shapes, for the segments are shown in FIG. 3B. For example, the shapes may be 1) cuboid, 2) pyramid, 3) a combination of a cuboid and pyramid, 4) a triangular prism, 5) a combination of a cuboid and a triangular prism. The combination of a cuboid and a triangular prism is shown in FIG. 3A, where the cuboid forms a base for the triangular prism.

In an aspect of the disclosure, each segment of the segmented light guide is offset from the optical sensor. In some aspects, the offset is by a scintillator module. In this aspect of the disclosure (and with a 4-to-1 module to sensor coupling), each scintillator module shares light with other scintillator modules from different optical sensors (pixels). For example, when optical photons enter the prismatoid (segment of the light guide) following a gamma ray interaction with a scintillator module 205, the photons (i.e., particles 300) are efficiently redirected to neighboring scintillator modules (of different pixels) due to the geometry, enhancing the light sharing ratio between optical sensors (pixels).

Figure 2B:
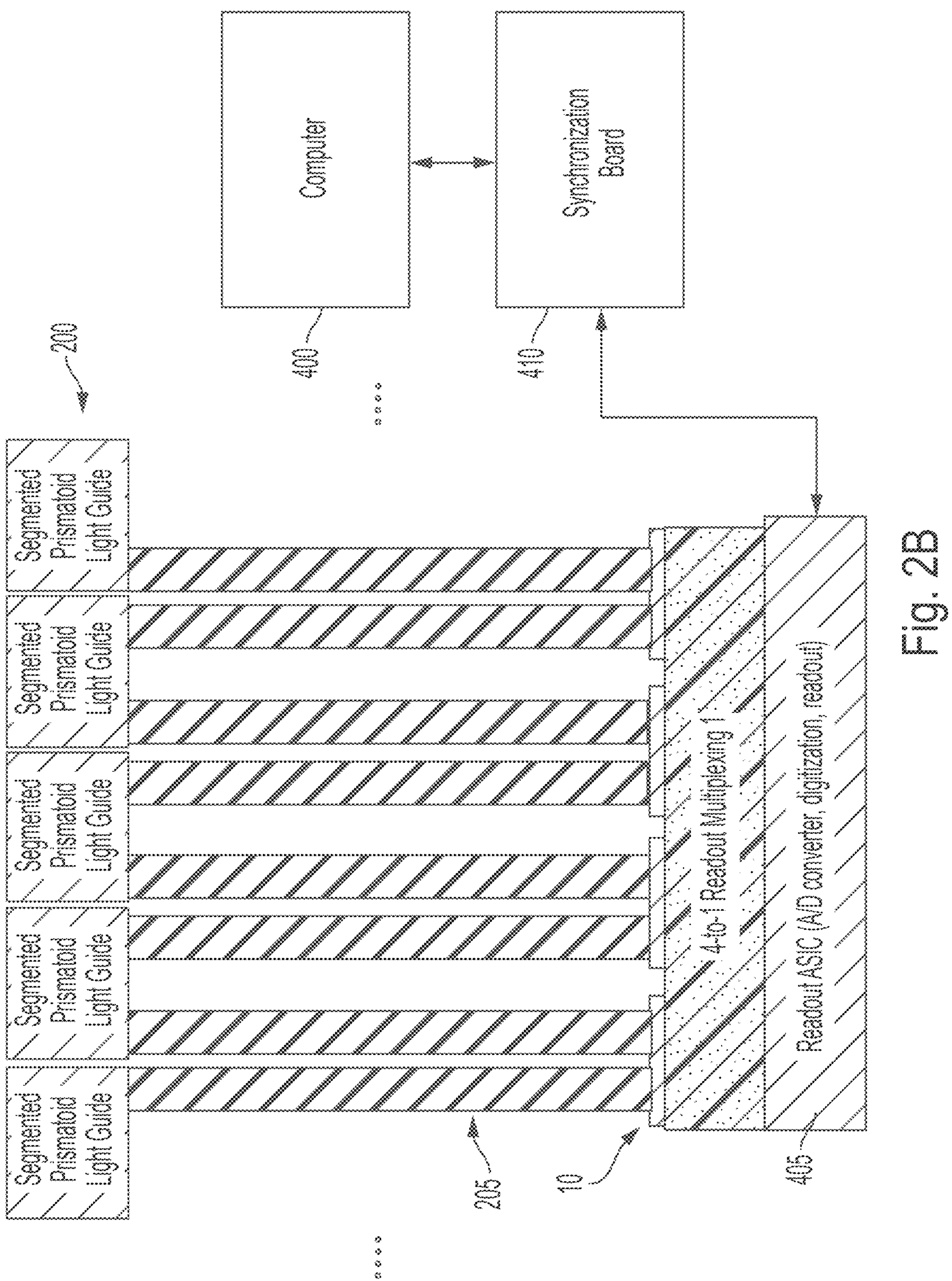
FIG. 2B illustrates a particle detection system in accordance with aspects of the disclosure, where there is a 4-to-1 scintillator module to optical sensor coupling.
Figure 4:
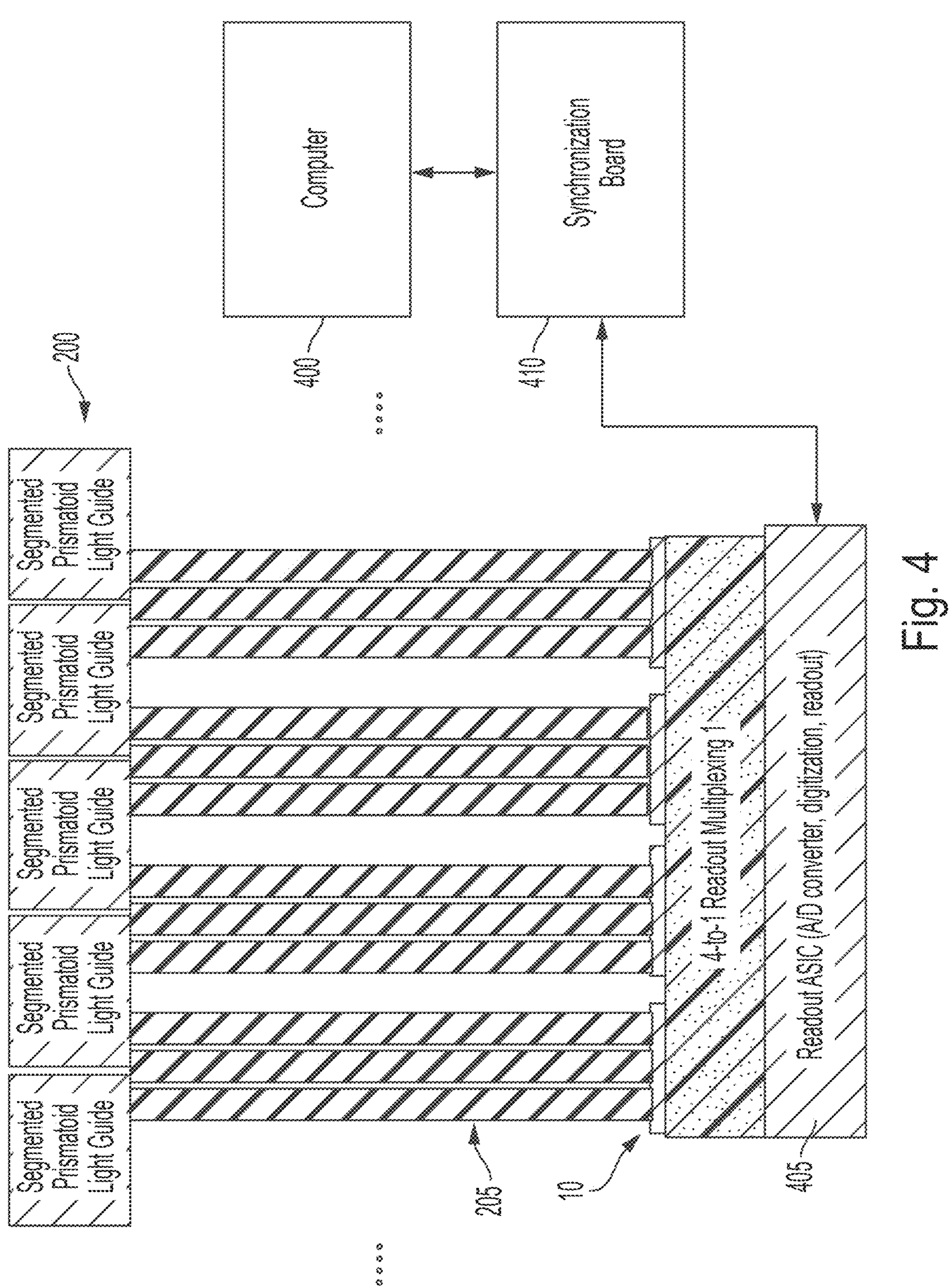
FIG. 4 illustrates a particle detection system in accordance with aspects of the disclosure, where there is 9-to-1 scintillator module to optical sensor coupling.

FIG. 4 illustrates another example of a particle detection system in accordance with aspects of the disclosure. In FIG. 4, there is a 9-to-1 scintillator module to optical sensor coupling. The optical sensors 10 are connected to the readout ASIC 405 in the same manner as described above 4-to-1 readout multiplexing 1 (as shown in FIGS. 1A and 2B). Similar to FIG. 2B, the readout ASIC 405 is connected to the computer 400 via the synchronization board 410. The synchronization board synchronizes readouts from different detection devices/Readout ASIC in the PET system.

In the system shown in FIG. 4, only one detection device is shown, however, in practice there are a plurality of detection devices connected to the synchronization board 410. Each detection device having the 4-to-1 readout multiplexing 1 described herein. The reflector 215 is omitted from FIG. 4. However, each detection device would have the reflector 215. The computer 400 may comprise at least one processor, a memory and a user interface such as a keyboard or/display. The user interface may be used by an operator to specify a readout interval or period.

Figure 5:
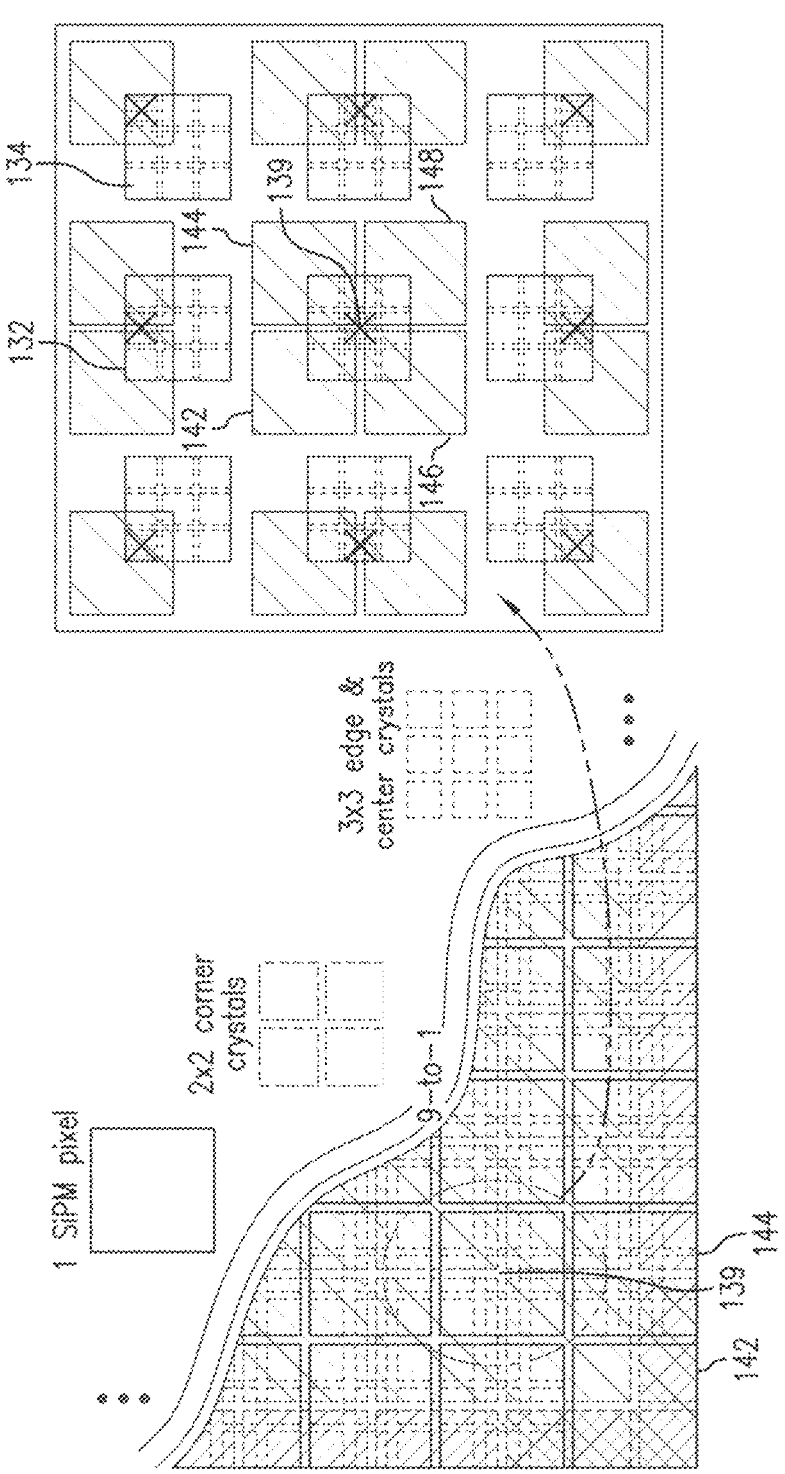
FIG. 5 illustrates a top-down view of a segmented light guide and optical sensors for a 9-to-1 scintillator module to optical sensor coupling, where there are three different designs of segments of the segmented light guide.

In an aspect of the disclosure, each pixel (other than the four corner pixels) may have nine scintillator modules 205. The corner pixels may have four scintillator modules. FIG. 5 shows the segments of the light guide. Similar to FIG. 3A, the different designed segments are shown in the bottom left with different hashing. The bottom left portion of FIG. 5 only shows a representative portion of the array 220. The solid lines around a group of scintillator modules or crystals in the bottom left refers to a pixel (SiPM pixel), whereas the dash lines refers to the modules or crystals. The three different designs for the prismatoid segments, e.g., center prismatoid 162, corner prismatoid 166 and edge prismatoid 168, are shown with different hashing. The center prismatoid 162 and edge prismatoid 168 are shown with hashing in opposite directions and the corner prismatoid 166 is shown with intersecting hashing. The profile of the corner prismatoid 166 for the 9×1 configured may be different from the 4×1 configured since only the corner pixels may have a 4×1 coupling in the 9×1 configuration. The right side of FIG. 5 illustrates several different center prismatoid positions with respect to the pixels (and scintillator modules). Not all SiPM pixels (optical sensors) are shown in the right side of FIG. 5. In FIG. 5, nine center prismatoids are shown to illustrate nine different primary interaction scintillator modules (primary interaction). For example, when the primary interaction scintillator module is module 139 (the center scintillator module in the segment), the segment directs the particles to four adjacent optical sensors/pixels 142, 144, 148, 148. The “X” in FIG. 5 refers to the primary interaction scintillator modules. Segments 132 and 134 may not be adjacent to each other but appear adjacent in the figure.

The corner prismatoid 166 in this configuration may redirect particles between ends of a group of five scintillator modules (three different optical sensors/pixels) (end in contact with the segment). An edge prismatoid in this configuration may redirect particles between ends five scintillator modules as well (two different optical sensors/pixels) (end in contact with the segment).

In other configurations, even the corner optical sensors/pixels 10 may be in contact with nine scintillator modules 205.

In an aspect of the disclosure, the scintillator modules 205 may have a tapered end as described in PCT Application Serial No. US21/48880 filed Sep. 2, 2021, entitled “Tapered Scintillator Crystal Modules And Methods Of Using The Same” the contents of which are incorporated by reference. The end that is tapered is the first end, e.g., scintillator module/optical sensor interface.

Figure 6:
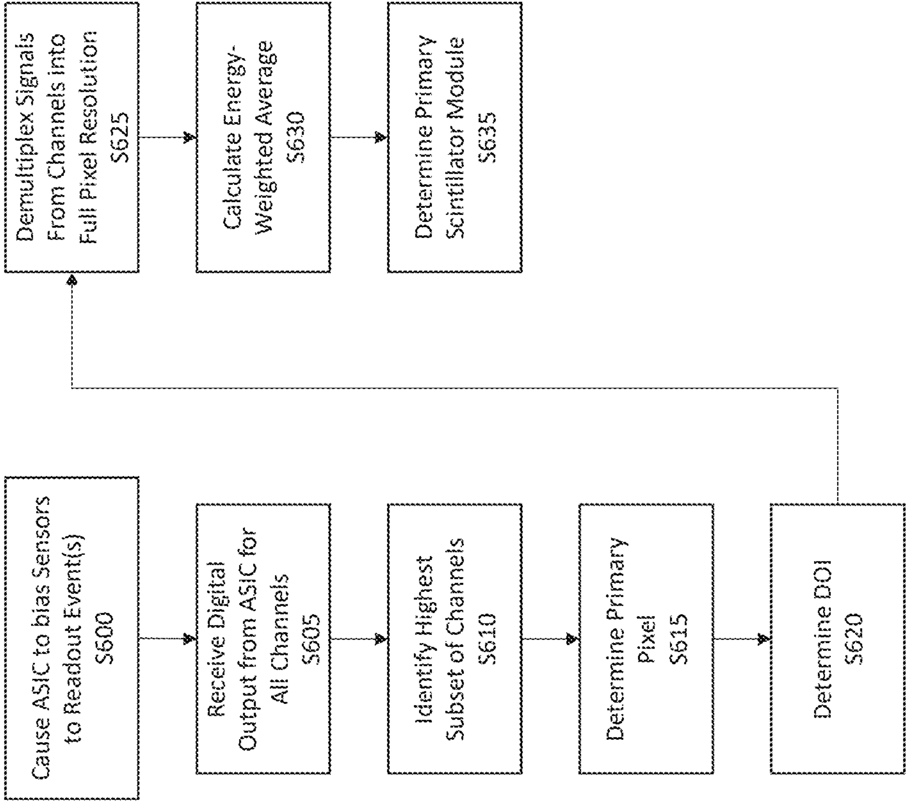
FIG. 6 illustrates a flow chart of a method in accordance with aspects of the disclosure.

FIG. 6 illustrates a flow chart of a method in accordance with aspects of the disclosure. For purposes of the description the functionality describe below is executed by a processor of the computer 400. At S600, the processor issues an instruction to the readout ASIC 405 (via the synchronization board 410) to readout signals from the optical sensor array. This may be in the form of a frame synchronization command. When the readout ASIC 405 receives the instruction, the readout ASIC 405 causes power to be supplied to the optical sensor array 210. In some aspects of the disclosure, there is a switch that is controlled to close to supply a bias. The readout ASIC 405 receives the multiplexed signals from the channels X01-X16 respectively (via the channel connections). The multiplexed signals are digitized and synchronized (via the synchronization board 410) and transmitted to the computer 400. In an aspect of the disclosure, the computer 400 comprises a communication interface. In some aspects, the communication interface may be a wired interface.

At S605, the processor receives the digitized signals from each of the channels. In some aspects of the disclosure, digitized signals are associated with a channel identifier such that the processor may recognize which digitized signals corresponds to which channel. The digitized signals may be stored in the memory. In an aspect of the disclosure, the computer 400 has a preset mapping identifying which pixels are connected to a respective channel (multiplexed). The mapping may be stored in the memory.

At 610, the processor may identify a subset of channels having the highest digitized signals, e.g., highest X energies, for the event (per event). Each event is determined with respect to a time window. The window for an event begins with an initial SiPM sensing a particle(s). The window is “open” for a set period of time. The set period of time may a few nanoseconds. Particles detected within the window (from any SiPM) are grouped and considered as belonging to the same event. In an aspect of the disclosure, the number of relevant channels may be based on the location of the event. For example, where the primary interaction is located in the center of the array (associated with a center prismatoid 162), the number of relevant channels may be four. The processor may identify the four channels having the four highest digitized signals for the event. When the primary interaction is located at a corner prismatoid 166, the processor may only need to identify three channels associated with the three highest digital output. When the primary interaction is located at the edge prismatoid 168, the processor may only need to identify two channels associated with the two highest digital output.

Given that the light sharing is optically isolated by the segments, the primary optical sensor (pixel) of interaction, may be determined from the relationship of the channels with the certain highest digitized signals. The relationship allows for the unique identification of adjacent optical sensors based on the pattern of the channels with the certain highest digitized signals. At S615, the processor may determine the primary interaction optical sensor (pixel). For example, in a case where the primary interaction optical sensor is a center, the processor may determine the relative locations of the identified four channels associated with the four highest signals using the stored mapping. This will narrow the primary optical sensor down to the four neighboring optical sensors/pixels (from the 16 possible sensors/pixels connected to the identified channels). For example, when the four highest channels are X02, X03, X10 and X11. The processor may identify SiPM pixels, 10, 11, 18 and 19 as the adjacent optical sensors, e.g., adjacent pixels. Then, the processor may determine which of the four channels had the highest signal. The optical sensor (out of the four neighboring optical sensors which were narrowed down) associated with the channel having the highest sensor, is identified as the primary optical sensor/pixel (primary interaction). For example, when the maximum signal of the four channels is X03, the processor may determine that the primary interaction optical sensor (pixel) is 19 (which was narrowed down from 17, 19, 21 and 23 connected to channel X03).

In a case where the primary interaction optical sensor is a corner, the processor may determine the relative locations of the identified three channels associated with the three highest signals using the stored mapping. In other aspects, the processor may still use the four channels with the four highest signals. This will narrow the primary interaction optical sensor down to three neighboring optical sensors/pixels. Then, the processor may determine which of the three channels had the highest signal. The optical sensor (out of the three neighboring optical sensors which were narrowed down) associated with the channel having the highest sensor, is identified as the primary optical sensor/pixel (primary interaction).

In a case where the primary interaction optical sensor is an edge optical sensor (associated with the edge prismatoid), the processor may determine the relative locations of the identified two channels associated with the two highest signals using the stored mapping. In other aspects, the processor may still use the four channels with the four highest signals. This will narrow the primary interaction optical sensor down to two neighboring optical sensors/pixels. Then, the processor may determine which of the two channels had the highest signal. The optical sensor (out of the two neighboring optical sensors which were narrowed down) associated with the channel having the highest sensor, is identified as the primary interaction optical sensor/pixel.

At S620, the processor may determine the DOI. The DOI may be determined using the following equation:

$$w = \frac{P\max}{P} \tag{1}$$

Pmax is the digitized value associated with the channel having the highest signal (highest energy) for the event and P is the sum of the digitized signals associated with the identified subset of channel for the event, which may also be calculated after subtracting out Pmax if desired. Since the segments optically isolate the adjacent optical sensors associated with the segment, the summation is effectively taking the ratio of the energy associated with the primary interaction optical sensor and the sum of the energy of the adjacent sensors. Once the processor identifies the primary interaction optical sensor, then it knows how many channels (highest M channels) to add, e.g., 4 for the optical sensors for the center prismatoid, 3 for the optical sensors for the corner prismatoid and 2 for the optical sensors for the edge prismatoid.

The ratio may then be converted into a depth using the following equation.

$$\mathrm{DOI}=m*w+q \tag{2}$$

where m is the slope between DOI and w according to a best-fit linear regression model, and q is the intercept to ensure DOI estimation starts at DOI=0 mm. Parameters m and q may be determined in advance for the scintillator modules 205.

Therefore, in accordance with aspects of the disclosure, the multiplexed signals may be used to determine the DOI and the primary interaction optical sensor without a need to demultiplex the signals using the demultiplexing techniques described herein such a machine learning or a look up table. In other aspects of the disclosure, the DOI may be calculated after the multiplexed signals are demultiplexed in accordance with aspects of the disclosure and subsequently calculated from the demultiplexed signals, where Pmax is the digitized value associated with the optical sensor/pixel having the highest demultiplexed value and p is the sum of all of the demultiplexed values for each optical sensor/pixel.

In an aspect of the disclosure, the primary interaction scintillator module made be estimated using the multiplexed signals based on the relative magnitudes of the four highest channels. Using the above identified example, when the four highest channels was X02, X03, X10 and X11, given the light sharing scheme for a center light segment (e.g., prismatoid), the top left scintillating module associated with SiPM 19 may be estimated to be the primary interaction scintillator module. Using the relative magnitudes, the processor may identify the primary optical sensor (pixel), vertical/horizontal neighbors and diagonal neighbors. A diagonal neighbor may have the lowest energy of the identified subset of channels. The horizontal/vertical neighbors may have a close energy, e.g., channel output may be nearly equal. The adjacent optical sensors identified using the subset of channels may be associated with the same segment (due to the light sharing).

While the primary interaction optical sensor and primary interaction scintillator module may be estimated as described above, due to scattering and noise, the same may be determined after the signals in the channels are demultiplexed as described herein, At S625, the processor may demultiplex the multiplexed signals from the channels into a full optical sensor resolution. For example, the processor takes the multiplexed signals from the 16 channels X01-X16 and generates M x M channels of information (number of optical sensors in the system), where M is the number of rows and columns. For example, for a 8×8 readout array, there are 64 demultiplexed channels.

In an aspect of the disclosure, the conversion is based on a prestored machine learned model. Generating the machine learned model will be described in detail with respect to FIGS. 7 and 8 later. Specifically, the processor may retrieve the stored machine learned model and using the multiplexed signals as inputs to output corresponding 64 channels of demultiplexed signals corresponding to the 8×8 array.

In other aspects, the processor may use a stored look up table which correlates the multiplexed signals into demultiplexed signals of full channel resolution. The look up table may be created using experimental data obtained from non-multiplexed channels. For an 8×8 array, the look up table may be created from 64 channels of experimental data taken from a plurality of events. For example, data from the 64 channels for an event is obtained. Multiplexed data may be generated by the processor (software-based multiplexing) which adds the same channels as shown in FIG. 1A to generate 16 channels of data (4 channels are added). The 16 channels of data are then associated with the 64 channels of data for later use. This process may be repeated for a plurality of events to create multiple correspondence information, e.g., 64 channels to 16 channels. Subsequently, when the multiplexed data is obtained from the readout ASIC 405, the processor looks up the 64 channel data. The processor may select the 64 channel data that corresponds with the 16 channel data that is the closest to the actual detected channel data. The closest may be defined as the smallest root mean square error or mean square error. However, other parameters may be used to determine the closest stored 16 channel data in the look up table. In other aspects of the disclosure, the processor may interpolate the 64 channel data based on the difference between the closest stored 16 channel data sets (e.g., two closest).

At S630, the processor, using the demultiplexed signals (e.g., signals representing the energy from each optical sensor, to calculate the energy weighted average). The energy weighted average may be calculated by the following equations:

$$u = \frac{1}{P}\sum_{i}^{N} x_i p_i \quad (3)$$

$$v = \frac{1}{P}\sum_{i}^{N} y_i p_i \quad (4)$$

where $x_i$ and $y_i$ are the x- and y-positions of the i-th readout optical sensor (pixel, $p_i$ is the digitized signal readout by the i-th optical sensor (pixel), N is the total number of optical sensors (pixels) in the optical sensor array and P is the sum of the digitized signals from all of the optical sensors (pixels) for a single gamma ray interaction event.

At S635, the processor may determine the primary interaction scintillator module based on the calculated energy weighted average for each scintillator module 205. The scintillator module 205 with the highest calculated energy weighted average may be determined as the primary interaction scintillator module. The optical sensor (pixel) associated with the scintillator module 205 with the highest calculated energy weighted average may be determined as the primary interaction optical sensor (pixel).

In other aspects of the disclosure, instead of determining all three features, e.g., the primary interaction optical sensor (pixel), the primary interaction scintillator module and the DOI, the processor may only determine one of the three features or any combination of the features, e.g., at least one of the three features.

Figure 7:
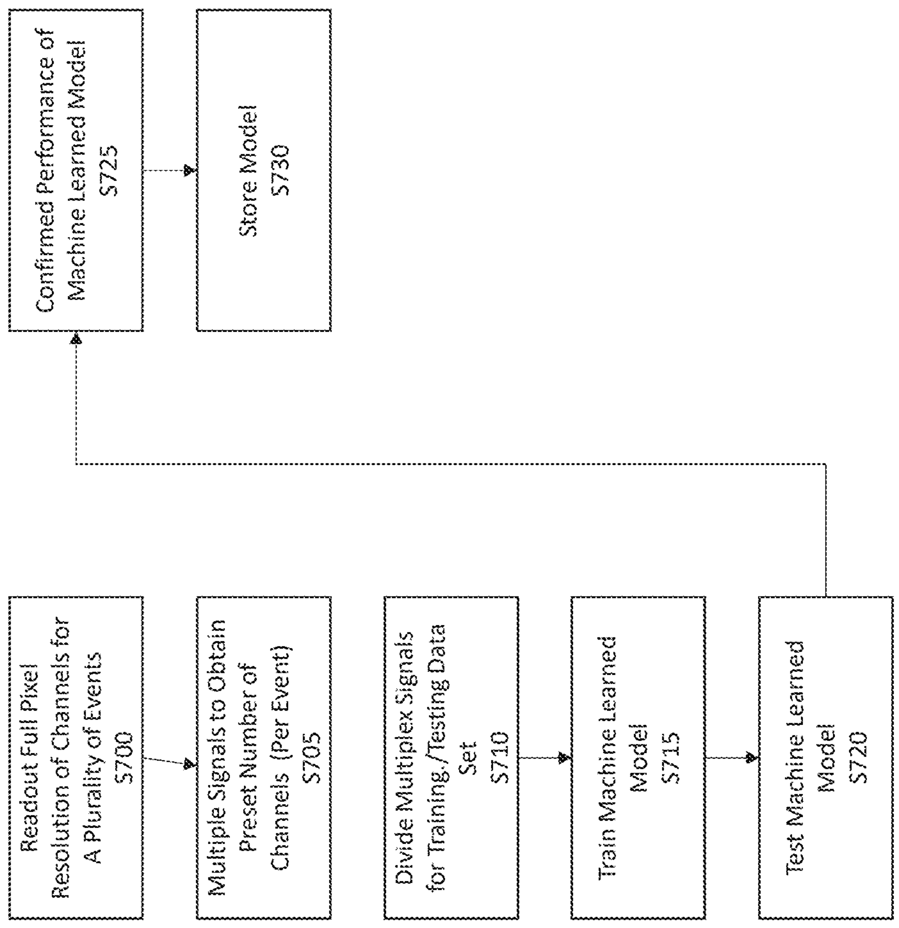
FIG. 7 illustrates flow chart of an example of training and testing of a machine learning model in accordance with aspects of the disclosure.

FIG. 7 illustrates flow chart of an example of training and testing of a machine learning model in accordance with aspects of the disclosure. The generation of the machine learning model(s) may be executed on the computer 400. In other aspects, a different device may execute the generating of the models and the models subsequently transmitted to the computer 400.

A different machine learning model may be used for different scintillator module/optical sensor array configurations. For example, a first machine learning model may be used for a 4-to-1 scintillator module to optical sensor array coupling and a second machine learning model may be used for a 9-to-1 scintillator module to optical sensor array coupling (and a third for a 16-to-1 coupling).

A different machine learning model may be used for different scintillator modules (dimensions). For example, with the same coupling (e.g., 4-to-1 scintillator module to optical sensor array coupling, different ML models may be used for scintillator modules having a 1.5 mm×1.5 mm×20 mm verses 1.4 mm×1.4 mm×20 mm. To obtain a dataset for training/testing, the particle detection device including the array of scintillator modules, the segmented light guide and optical sensor array (connected to a readout ASIC) may be exposed to a known particle source. Instead of being multiplexed in accordance with aspects of the disclosure via the connections to the readout ASIC, the optical sensor array is connected to the readout ASIC via N connections, where N is the number of optical sensors in the optical sensor array. The device may be exposed at different depths and over a plurality of events. The digitized signals from each channel (e.g., 64 channels) is recorded per event at S700. This full channel resolution is taken as the ground truth for evaluating the model (during testing).

At S705, multiplex signals may be generated by adding a preset number of channels for each event. In an aspect of the disclosure, a processor adds the signals from the same optical sensors in accordance with the multiplexing scheme depicted in FIG. 1A to get the multiplex signals. This is to simulate the hardware multiplexing described herein. For example, the processor may add the signals from four optical sensors together to reduce the number of channels to 16. The computer-based multiplexed signals may be stored in a memory. At S710, the processor divides the computer-based multiplexed signals, generated for each event into a dataset for training and a dataset for testing. In some aspects, 80% of the computer-based multiplexed signals may be used for training and 20% may be used for testing and validation. Other divisions may be used such as 75%/25% or 90%/10%. In some aspects, the division may be random.

The machine learning model may be neural network based. However, the machine learning model is not limited to the NN. Other machine learning techniques may be used such as state vector regression. In some aspects of the disclosure, the neural network may be a convolution neural network (CNN). Additionally, in some aspects of the disclosure, the CNN may be a shallow CNN having a U-NET architecture. The hyperparameters including number of convolutional layers, filters and optimizer may be optimized iteratively.

Figure 8:
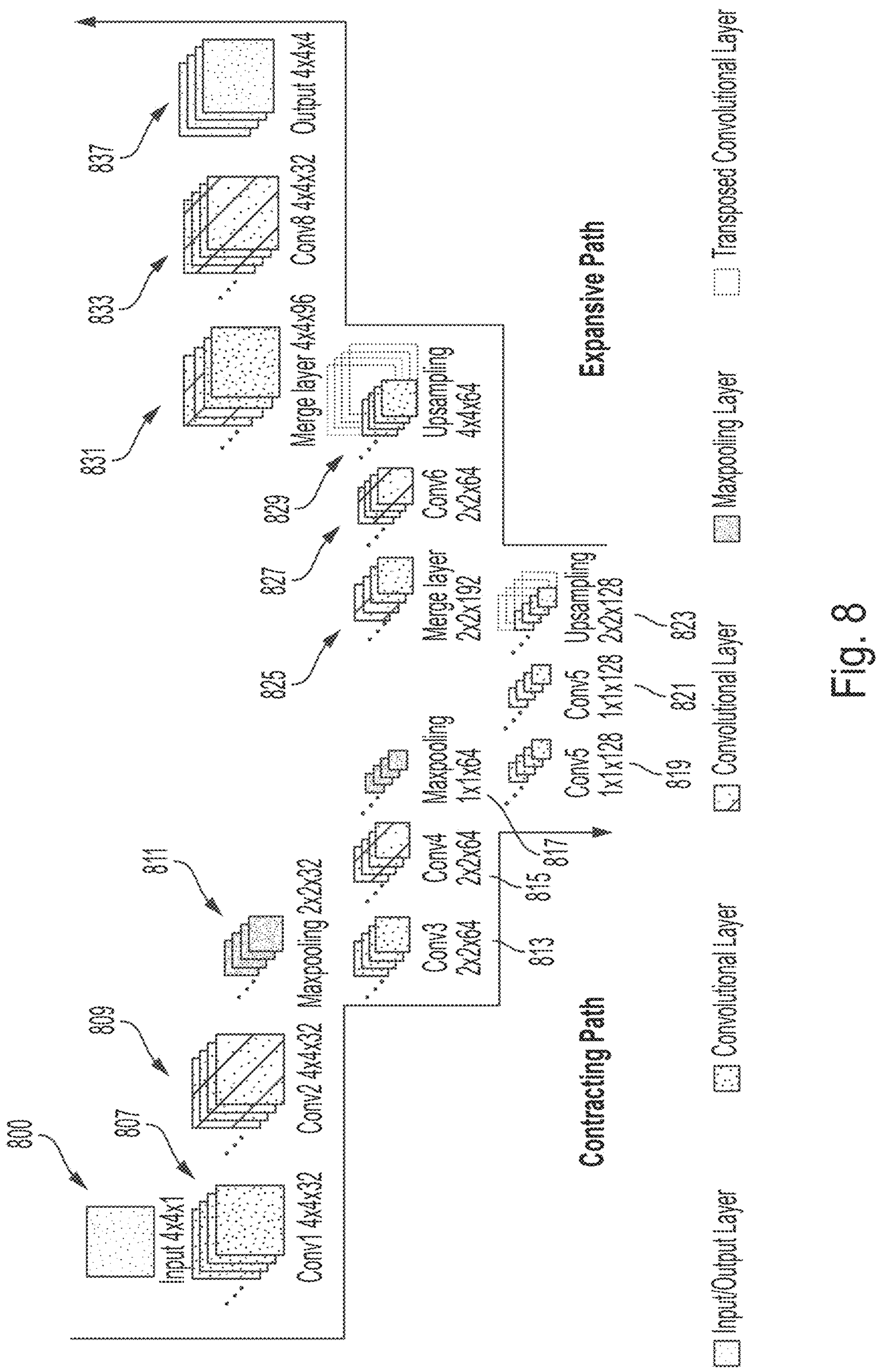
FIG. 8 illustrates an example of a machine learning model in accordance with aspect of the disclosure.

FIG. 8 illustrates an example of the CNN having the U-NET architecture.

The U-Net consisted of an input layer 800 with the multiplexed data (16×1 which may be reshaped into a 4×4×1 matrix before feeding into the CNN). The input layer 800 may be follows by a series of 2D convolutions such as 807/809 such in FIG. 8. Convolutional layers 807 and 809 may have 32 different 4×4 matrices (also known as "filters").

The convolutional layer 807/809 may be followed by a max-pooling layer 811 to reduce its 2D dimensionality to 2×2, additional convolutional layers 813/815 with 64 filters each, and another max-pooling layer 817 to reduce 2D dimensionality to 1×1. After being reduced to 1×1 dimension space, the matrices may go through several convolutional layers 819/821 with 128 filters each, before undergoing an expansive path to bring it back to its original 4×4 dimensionality and complete the "U" shape.

The expansive path comprises a series of upsampling convolutional layers 823/829 with feature merging with the corresponding layers with equal dimensionality 825/831 and convolutional layers 827/833 with 64/32 filters, respectively. The output layer 837 may be a convolutional layer with 4 filters to provide a 4×4×4 matrix, which may be then reshaped to correlate with the 8×8 readout array. All convolutional layers in the U-Net may have 2×2 filters with stride=1 and may be followed by rectified linear unit (ReLU) activation function. Conceptually, the U-Net may be formulated to demultiplex the single 4×4 matrices (computer-based multiplexed signals) that were fed into the input layer into 8×8 matrices (demultiplexed), which is equal to the number of optical sensors in the array. Note that the shape of the input layer (dimensionality of the matrix) and number of filters in the output layer may be modified based on the readout array being used. For example, the input matrix may be 16×1. Additionally, multiplexed input matrices may be used having smaller dimensions.

The above model may be trained using the training dataset at S715 where the training dataset is input at 800. The above model may be tested using the testing dataset at S720 where the testing dataset is input at 800. The optimizer may be a modified version of Adam optimizer. The initial learning rate may be 1.0. The performance of the model may be evaluated using an evaluation parameter at S725. For example, the evaluation parameter may be mean-squared error MSE. However, the evaluation parameter is not limited to MSE.

Once the model is confirmed using the evaluation parameter, the model may be stored in a memory (in the computer 400) or transmitted to the computer 400 at S730 for subsequent use.

The multiplexing scheme described in FIG. 1A and demultiplexing using machine learning model(s) was tested for both a 4-to-1 scintillator module and optical sensor array coupling and a 9-to-1 scintillator module and optical sensor array coupling.

The scintillator modules were fabricated using LYSO and were coupled to an 8×8 SiPM array (optical sensor array) on one end and the prismatoid segmented light guide as described above on the other end. The scintillator module array for the 4-to-1 scintillator module and optical sensor array coupling consisted of a 16×16 array of 1.4 mm×1.4 mm×20 mm, while the scintillator module array for the 9-to-1 scintillator module and optical sensor array coupling consisted of a 24×24 array of 0.9 mm×0.9 mm×20 mm.

Standard flood data acquisition was acquired from both scintillator module arrays (and sensors) by uniformly exposing them with a 3MBq Na-22 sodium point source (1 mm active diameter) place 5 cm away (at different depths). Depth-collimated data at 5 different depths along the 20 mm scintillator module length (2, 6, 10, 14 and 18 mm) was acquired using lead collimation (1 mm pinhole) to evaluate DOI performance. Data readout was expedited with an ASIC (TOFPET2) and a FEB/D_v2 readout board (PETsys Electronics SA). Computer-based multiplexing was done as described above to achieve a 16×1 scintillator module to channel multiplexing for the 4-to-1 scintillator module to optical sensor coupling and a 36×1 scintillator module to channel multiplexing for the 9-to-1 scintillator module to optical sensor coupling.

Photopeak filtering using the computer-based multiplexing was performed on a per scintillator module basis with a +−15% energy window. Only events where the highest signal was greater than twice the second signals were accepted in order to reject Compton scatter events with the photopeak.

Demultiplexing the signals generated via the computer-based multiplexing was done using the method described above via the machine learning (CNN with U-Net architecture). U-Net training was carried out using 80% of the total dataset. 10% of the training dataset was held out and used for training validation to ensure overfitting wasn't occurring. Adadelta, a modified version of the Adam optimizer was used for training optimization.

A batch size of 500 and 1000 epochs were used for training. Training loss was calculated by taking the average difference between the model estimation and ground truth values across all events for each epoch. Model training was done to reduce loss between successive epochs until a global minimum was found. Model convergence was observed by plotting the training and validation loss curves as a function of epochs and ensuring that they reached asymptotic behavior with approximately equal minimums.

Figure 9A:
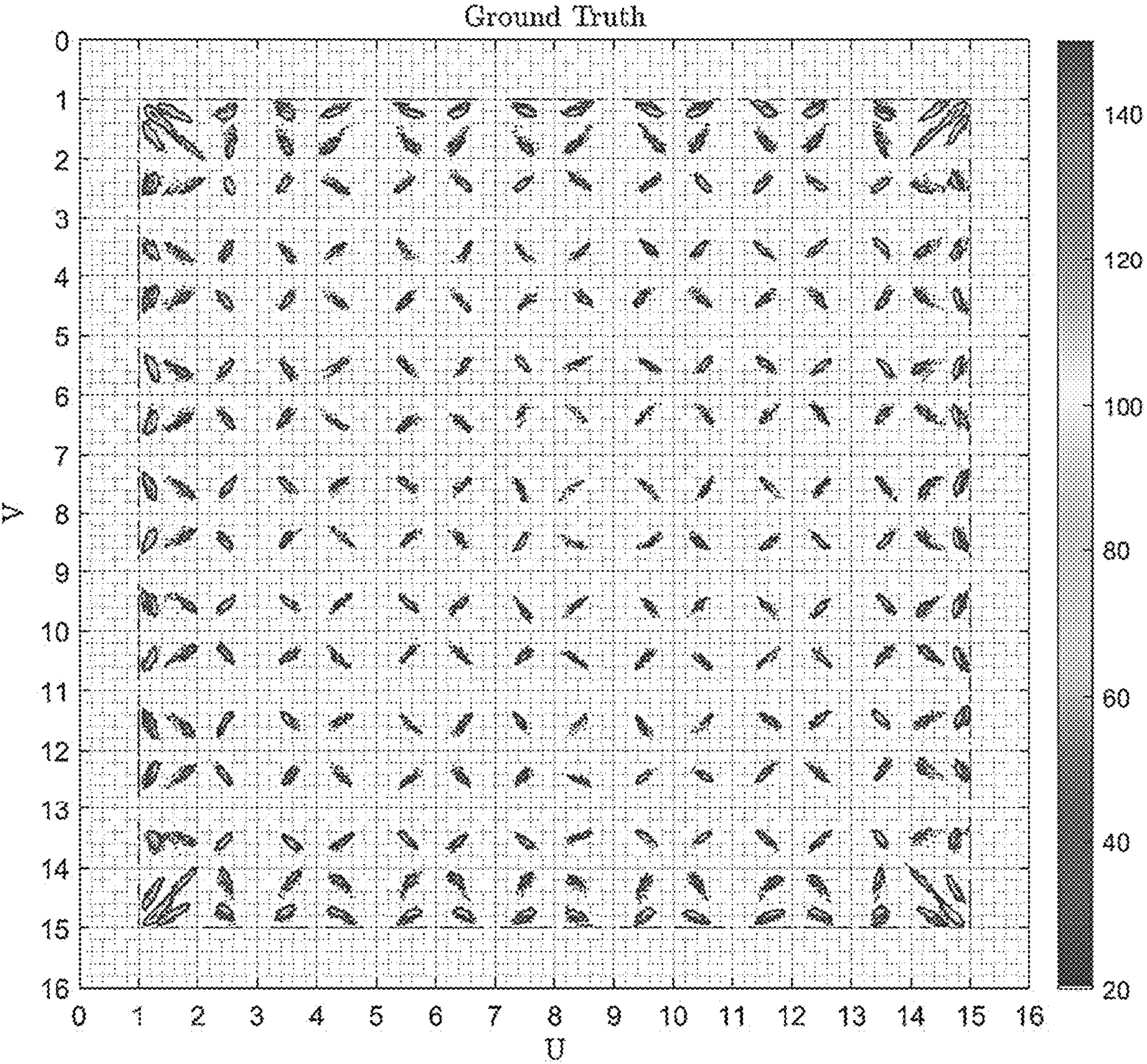

FIGS. 9A and 9B illustrate a qualitative comparison of the actual signals output from each of the plurality of optical sensor array (without multiplexing) and predictions obtained from the trained/tested machine learning model on computer-based multiplexed signals using the multiplexing scheme illustrated in FIG. 1A (demultiplexed) from the 4-to-1 scintillator module to optical sensor coupling. The results appear to be similar. For example, as comparison shown that perfect scintillator module separation was achieved in all center, edge and corner scintillator modules both with and without computer-based multiplexing (of the per-pixel channels). U is on the x-axis and V is on the y-axis.

Figure 9C:
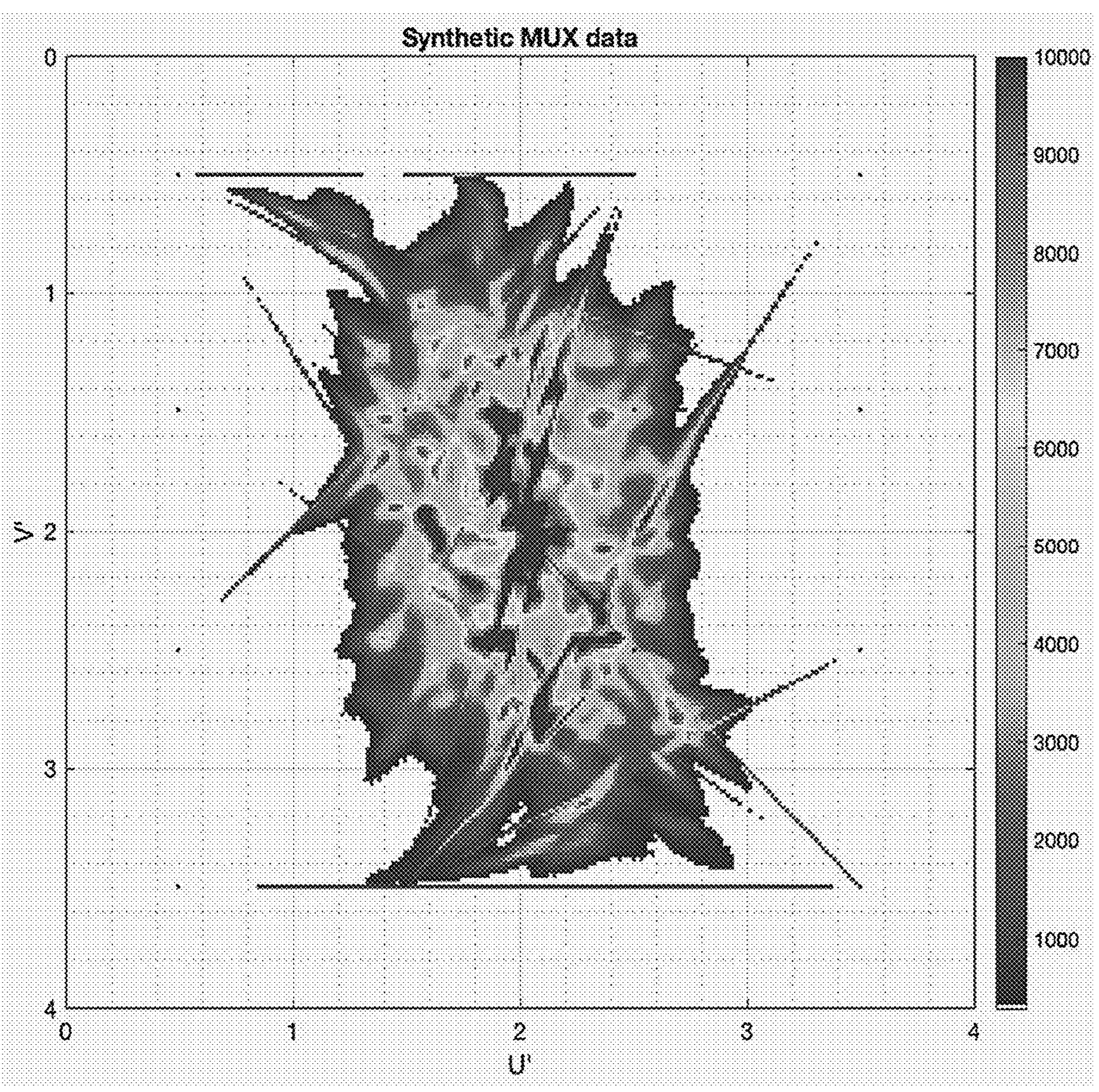
FIG. 9C and FIG. 9D illustrates a comparison between a synthetic multiplexed dataset and an actual multiplexed dataset multiplexed in accordance with aspects of the disclosure.
Figure 9D:
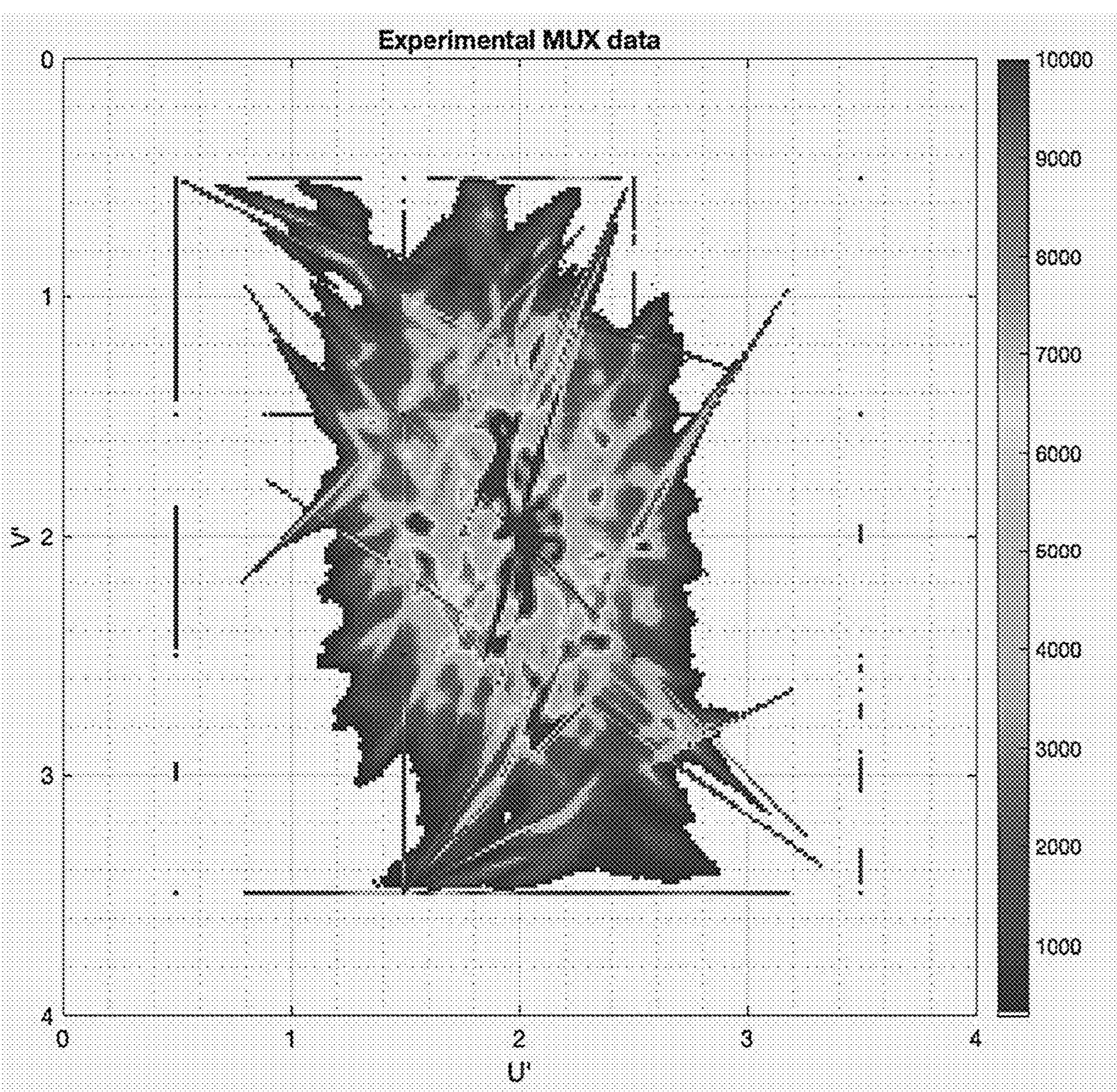

FIG. 9C shows an example of a synthetic dataset (computer-based multiplexed data) generated by added four sensor outputs in a similar manner described above (multiplexed) where a full resolution (e.g., 64) sensor outputs were read. FIG. 9D shows an example of multiplexed dataset generated from readout of multiplexed signals from a readout ASIC where the readout ASIC is connected to the array via the multiplexing scheme as described above. A comparison of FIG. 9C and FIG. 9D show that the datasets are very similar but slightly different due to imperfect model convergence. FIG. 9C and FIG. 9D show the mapping in U' and V' space which is done to show the channels in a square.

Figures 10A, 10B:
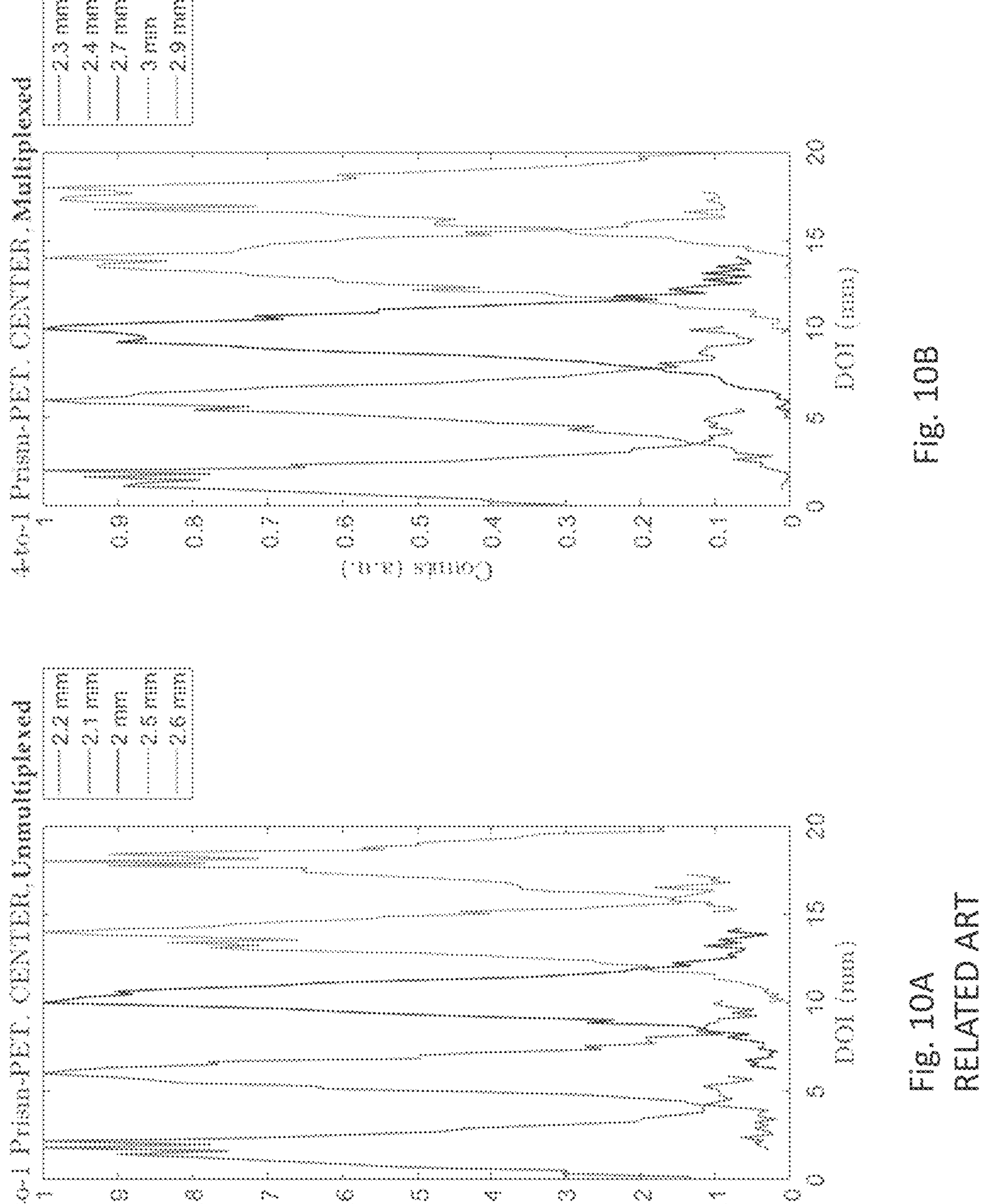
FIG. 10A and FIG. 10B illustrate a comparison between DOI resolution in a related particle detection system verses the DOI resolution of a particle detection system in accordance with aspect of the disclosure for a 4-to-1 scintillator module to optical sensor coupling.

FIG. 10A and FIG. 10B illustrate a comparison between DOI resolution in a related particle detection system verses the DOI resolution of a particle detection system in accordance with aspect of the disclosure for a 4-to-1 scintillator module to optical sensor coupling for the five different depths (2, 6, 10, 14 and 18 mm). The comparison is for a center optical sensor in the optical sensor array and another center optical sensor in the optical sensor array. In FIG. 10A, a "classical" calculation approach was used. In the classical approach, equation 1 was calculated using the highest energy signal (Pmax for the optical sensor or pixel basis) and the P was calculated from the sum of each channel (not multiplexed and therefore all 64 channel values were added). In FIG. 10B, the DOI was directly calculated by the computer-based multiplexed signals. For example, Pmax was determined as the highest signal from the 16 computer-based multiplexed signals and P was determined from the sum of the highest four signals from the 16 computer-based multiplexed signals.

The DOI estimation distribution were similar for the non-multiplexed data (FIG. 10A) and the multiplexed data (FIG. 10B). Average DOI resolution across all measured depths was 2.32 mm full-width at half-maximum (FWHM) for the non-multiplexed data (FIG. 10A) and 2.73 mm FWHM for the multiplexed data (FIG. 10B).

Figure 11A:
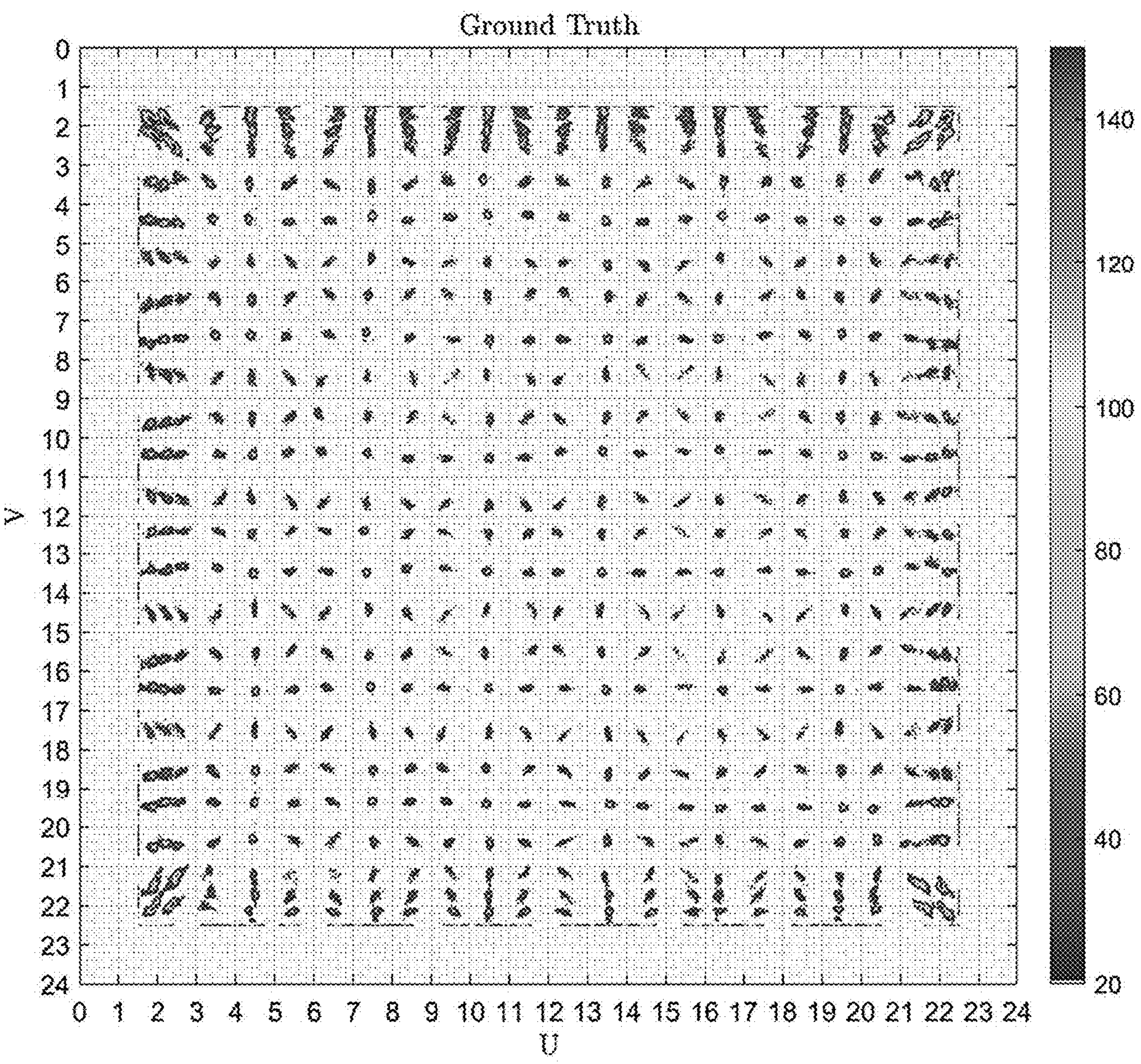
FIG. 11A and FIG. 11B illustrate a comparison between a ground truth and demultiplexing the multiplexed signals using the machine learning model in accordance with aspects of the disclosure for a 9-to-1 scintillator module to optical sensor coupling.
Figure 11B:
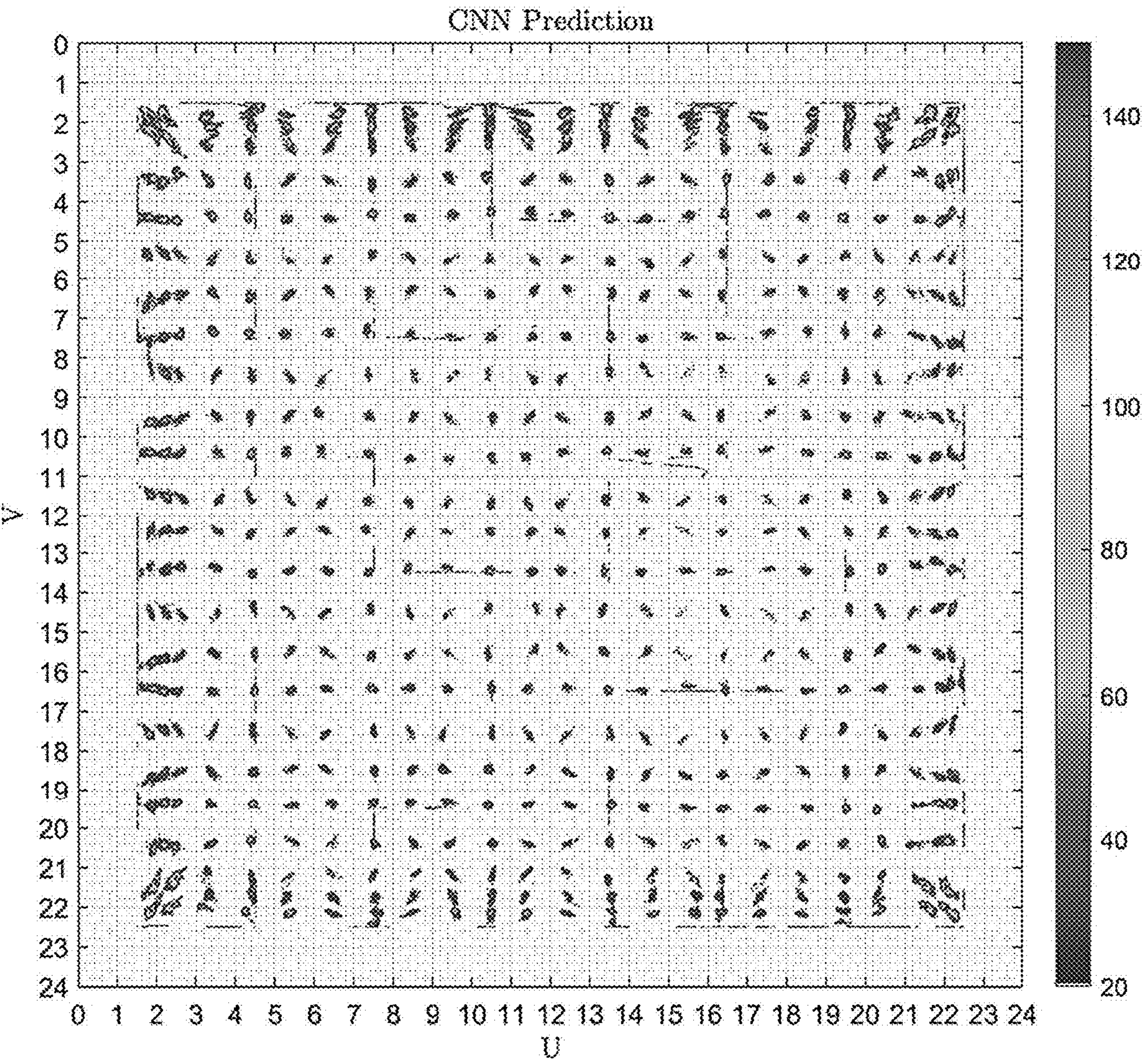

FIGS. 11A and 11B illustrate a qualitative comparison of the actual signals output from each of the plurality of optical sensor array (without multiplexing) and predictions obtained from the trained/tested machine learning model on computer-based multiplexed signals using the multiplexing scheme illustrated in FIG. 1A (demultiplexed) from the 9-to-1 scintillator module to optical sensor coupling. Excellent scintillator module separation was achieved in the center and edge scintillator modules with comparable performance between the non-multiplexed data (FIG. 11A) and the multiplexed data (FIG. 11B).

Figures 12A, 12B:
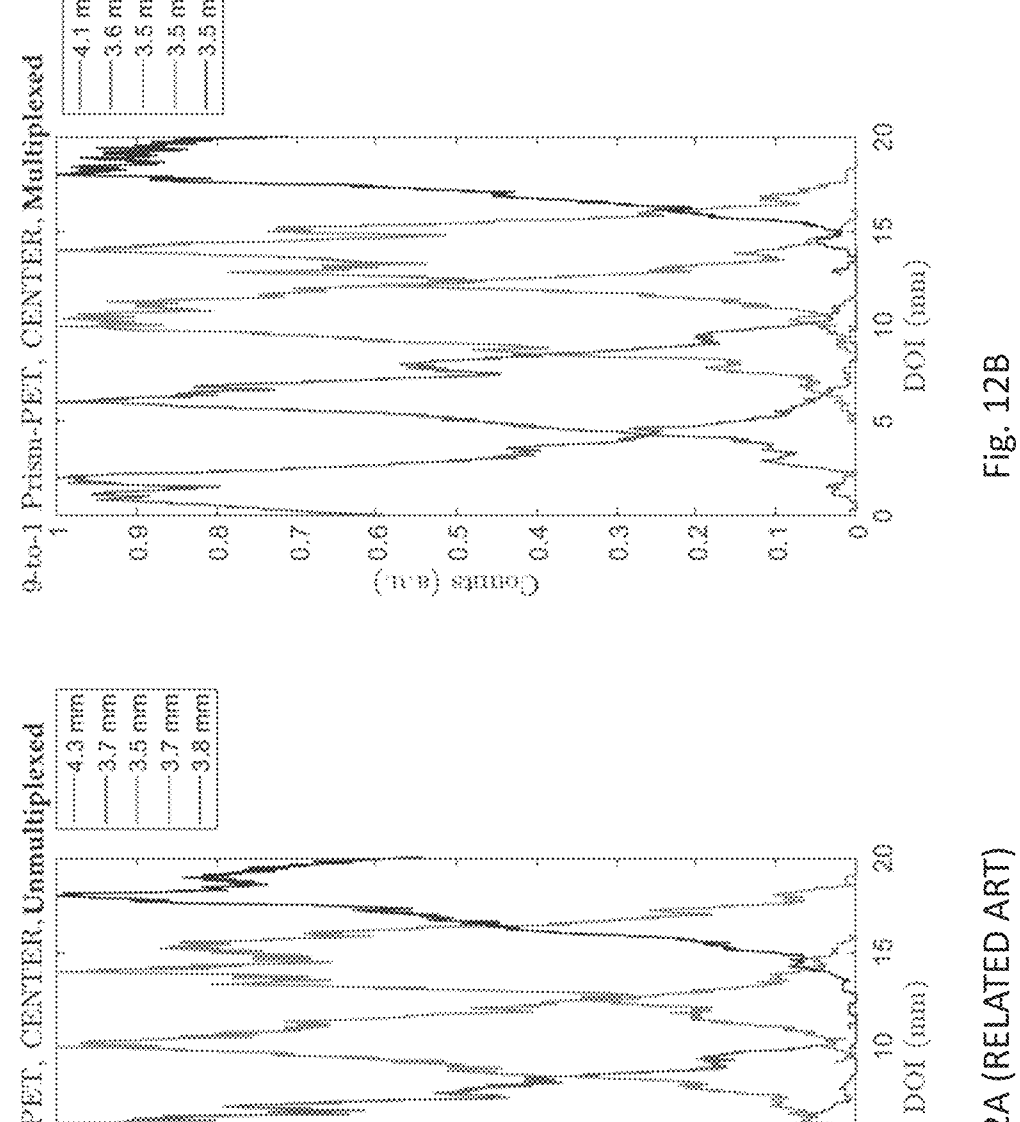
FIG. 12A and FIG. 12B illustrate a comparison between DOI resolution in a related particle detection system verses the DOI resolution of a particle detection system in accordance with aspect of the disclosure for a 9-to-1 scintillator module to optical sensor coupling.

FIG. 12A and FIG. 12B illustrate a comparison between DOI resolution in a related particle detection system verses the DOI resolution of a particle detection system in accordance with aspect of the disclosure for a 9-to-1 scintillator module to optical sensor coupling for the five different depths (2, 6, 10, 14 and 18 mm). The comparison is for a center optical sensor in the optical sensor array and another center optical sensor in the optical sensor array. In FIG. 12A, a "classical" calculation approach was used. In the classical approach, equation 1 was calculated using the highest energy signal (Pmax for the optical sensor or pixel basis) and the P was calculated from the sum of each channel (not multiplexed and therefore all 64 channel values were added). In FIG. 12B, the DOI was directly calculated by the computer-based multiplexed signals. For example, Pmax was determined as the highest signal from the 16 computer-based multiplexed signals and P was determined from the sum of the highest four signals from the 16 computer-based multiplexed signals.

The DOI estimation distribution were similar for the non-multiplexed data (FIG. 12A) and the multiplexed data (FIG. 12B). Average DOI resolution across all measured depths was 3.8 mm full-width at half-maximum (FWHM) for the non-multiplexed data (FIG. 12A) and 3.64 mm FWHM for the multiplexed data (FIG. 12B).

The percent error for CNN prediction with respect to energy-weighted average methods for x- and y-coordinates was 2.05% and 2.15%, respectively, for 4-to-1 scintillator module to optical sensor coupling, and 2.41% and 1.97% for 9-to-1 scintillator module to optical sensor coupling. The percent error for total detected energy per event for the multiplexed data following CNN prediction was 1.53% for 4-to-1 scintillator module to optical sensor coupling and 1.69% for 9-to-1 scintillator module to optical sensor coupling.

The above test demonstrates that any difference between the system's performance by using the described multiplexing scheme as depicted in FIG. 1A is minimal due to the deterministic light sharing which is a result of the prismatoid segmented light guide. It is noted that the observed difference may be a result of the experiment conditions such as using the 3MBq Na-22 sodium point source (1 mm active diameter). The multiplexing results the data output from the optical sensor array into the readout ASIC and connections. Minimizing the size of the data files is especially critical as the field shifts toward DOI PET, which depending on the readout scheme and DOI resolution (which determines the number of DOI bins), may increase the effective number of Lines of Response (LORs) by more than 2 orders of magnitude.

As used herein terms such as "a", "an" and "the" are not intended to refer to only a singular entity, but include the general class of which a specific example may be used for illustration.

As used herein, terms defined in the singular are intended to include those terms defined in the plural and vice versa.

References in the specification to "one aspect", "certain aspects", "some aspects" or "an aspect", indicate that the aspect(s) described may include a particular feature or characteristic, but every aspect may not necessarily include the particular feature, structure, or characteristic. Moreover, such phrases are not necessarily referring to the same aspect. Further, when a particular feature, structure, or characteristic is described in connection with an aspect, it is submitted that it is within the knowledge of one skilled in the art to affect such feature, structure, or characteristic in connection with other aspects whether or not explicitly described. For purposes of the description hereinafter, the terms "upper", "lower", "right", "left", "vertical", "horizontal", "top", "bottom", and derivatives thereof shall relate to a device relative to a floor and/or as it is oriented in the figures.

Reference herein to any numerical range expressly includes each numerical value (including fractional numbers and whole numbers) encompassed by that range. To illustrate, reference herein to a range of "at least 50" or "at least about 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" or "less than about 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc.

As used herein, the term "processor" may include a single core processor, a multi-core processor, multiple processors located in a single device, or multiple processors in wired or wireless communication with each other and distributed over a network of devices, the Internet, or the cloud. Accordingly, as used herein, functions, features or instructions performed or configured to be performed by a "processor", may include the performance of the functions, features or instructions by a single core processor, may include performance of the functions, features or instructions collectively or collaboratively by multiple cores of a multi-core processor, or may include performance of the functions, features or instructions collectively or collaboratively by multiple processors, where each processor or core is not required to perform every function, feature or instruction individually. For example, a single FPGA may be used or multiple FPGAs may be used to achieve the functions, features or instructions described herein. For example, multiple processors may allow load balancing. In a further example, a server (also known as remote, or cloud) processor may accomplish some or all functionality on behalf of a client processor. The term "processor" also includes one or more ASICs as described herein.

As used herein, the term "processor" may be replaced with the term "circuit". The term "processor" may refer to, be part of, or include processor hardware (shared, dedicated, or group) that executes code and memory hardware (shared, dedicated, or group) that stores code executed by the processor.

Further, in some aspect of the disclosure, a non-transitory computer-readable storage medium comprising electronically readable control information stored thereon, configured in such that when the storage medium is used in a processor, aspects of the functionality described herein is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term memory hardware is a subset of the term computer-readable medium.

The described aspects and examples of the present disclosure are intended to be illustrative rather than restrictive, and are not intended to represent every aspect or example of the present disclosure. While the fundamental novel features of the disclosure as applied to various specific aspects thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or aspects of the disclosure may be incorporated in any other disclosed or described or suggested form or aspects as a general matter of design choice. Further, various modifications and variations can be made without departing from the spirit or scope of the disclosure as set forth in the following claims both literally and in equivalents recognized in law.

What is claimed is:

1. A system for reading out signals from an optical sensor array, the optical sensor array comprising a plurality of optical sensors arranged in rows and columns, each optical sensor in the array corresponding to a pixel, the system comprises:

a plurality of first channels;

a plurality of second channels; and a first processor electrically connected to the plurality of optical sensors via the plurality of first channels and the plurality of second channels, each first channel being electrically connected to a subset of optical sensors in a corresponding row of the optical sensor array, where there is at least one optical sensor between connections, each second channel being electrically connected to a subset of optical sensors in a corresponding column of the optical sensor array, where there is at least one optical sensor between connections, where signals are readout by the first processor via the plurality of first channels and the plurality of second channels, and the first processor causes power to be supplied to each of the plurality of optical sensors to bias the optical sensors during a readout.

2. The system of claim 1, wherein the plurality of first channels comprises a first row channel and a second row channel, wherein the first row channel is electrically connected to a subset of optical sensors in a first row of the optical sensor array, and the second row channel is electrically connected to a subset of optical sensors in a second row of the optical sensor array, wherein the first row is adjacent to the second row, wherein the subset of optical sensors in the first row are not in the same columns of the optical sensor array as the subset of optical sensors in the second row.

3. The system of claim 1, wherein the plurality of second channels comprises a first column channel and a second column channel, wherein the first column channel is electrically connected to a subset of optical sensors in a first column of the optical sensor array, and the second column channel is electrically connected to a subset of optical sensors in a second column of the optical sensor array, wherein the first column is adjacent to the second column, wherein the subset of optical sensors in the first column are not in the same rows of the optical sensor array as the subset of optical sensors in the second column.

4. The system of claim 1, wherein the optical sensors are silicon photomultipliers (SiPMs) and there is at least one SiPM between the connections.

5. A particle detection device comprising the system of claim 1, wherein the device further comprising:

a scintillator array comprising a plurality of scintillator modules, the plurality of scintillator modules being greater than the plurality of optical sensors, where multiple scintillator modules are in contact with a respective optical sensor at a first end of the respective scintillator modules; and a segmented light guide comprising a plurality of prismatoid segments, the segmented light guide is in contact with a second end of the plurality of scintillator modules, each prismatoid segment being in contact with scintillator modules that are in contact with at least two different optical sensors, the at least two different optical sensors being adjacent optical sensors, and where each prismatoid segment is configured to redirect particles between scintillator modules in contact with the respective prismatoid segment.

6. The particle detection device of claim 5, wherein the prismatoid segments comprises: center prismatoid segments, edge prismatoid segments and corner prismatoid segments, wherein the center prismatoid segments are in contact with scintillator modules that are in contact with four adjacent optical sensors, corner prismatoid segments are in contact with scintillator modules that are in contact with three adjacent optical sensors and edge prismatoid segments are in contact with scintillator modules that are in contact with two adjacent optical sensors.

7. A particle detection system comprising:

the particle detection device of claim 5; and, a second processor in communication with the first processor, wherein the second processor is configured to identify a subset of channels having the highest signals per event and determine at least one of a primary interaction pixel for the event, a primary interaction scintillator module for the event or a depth of interaction of the event using signals from the identified subset of channels.

8. The particle detection system of claim 7, wherein the second processor is configured to determine the depth of interaction of the event based on a ratio of the signal from the channel having the highest signal per event and a sum of the signals from each of the subset of channels having the highest signals per event, respectively.

9. The particle detection system of claim 7, wherein the second processor is configured to determine the primary interaction pixel for the event based on positional relationship between the subset of channels to unique identify adjacent pixels and the channel having the highest signal per event to identify the primary interaction pixel from the identified adjacent pixels.

10. The particle detection systems of claim 9, wherein the second processor is configured to determine the primary interaction scintillator module using relative values of the signals from the identified subset of channels and the identified adjacent optical pixels.

11. The particle detection system of claim 7, wherein the second processor is configured to determine the primary interaction scintillator module for the event based on an energy weighted average.

12. The particle detection system of claim 11, wherein the second processor is configured to demultiplex signals from the plurality of first channels and the plurality of second channels using a stored machine learned model using the signals from the plurality of first channels and the plurality of second channels as input.

13. The particle detection system of claim 12, wherein the machine learned model is based on a convolutional neural network.

14. The particle detection system of claim 12, wherein the second processor is configured to calculate the energy weighted average using the demultiplexed signals.

15. The particle detection system of claim 12, wherein the second processor is configured to calculate the depth of interaction using the demultiplexed signals.

16. The particle detection system of claim 11, wherein the second processor is configured to demultiplex signals from the plurality of first channels and the plurality of second channels using a stored look up table.

17. The particle detection system of claim 7, wherein a number of channels in the subset of channels is based on the location of the primary optical sensor in the optical sensor array.

18. The particle detection system of claim 17, wherein the number of channels in the subset when the primary optical sensor is a corner optical sensor in the optical sensor array is three, the number of channels in the subset when the primary optical sensor is an edge optical sensor is two and the number of channels in the subset when the primary optical sensor is a center optical sensor in the array is four.

19. The particle detection system of claim 7, wherein there is a four-to-one scintillator module to optical sensor coupling.

20. The particle detection system of claim 7, wherein there is a nine-to-one scintillator module to optical sensor coupling.

* * * * *